US011877838B2

(12) United States Patent
Khayamian et al.

(10) Patent No.: US 11,877,838 B2
(45) Date of Patent: Jan. 23, 2024

(54) PREVENTING CYTOKINE STORM IN COVID-19 PATIENTS BY SUPPRESSING CLONAL EXPANSION IN ACTIVATED LYMPHOCYTES USING ALTERNATING ELECTRIC FIELDS

(71) Applicants: Mohammad Ali Khayamian, Tehran (IR); Mohammad Abdolahad, Tehran (IR); Hamed Abadijoo, Tehran (IR); Mahsa Faramarzpour Darzini, Tehran (IR); Mohammadreza Ghaderinia, Tehran (IR); Hossein Simaee, Tehran (IR); Seyed Mojtaba Yazdanparast, Tehran (IR); Shahriar Shalileh, Tehran (IR)

(72) Inventors: Mohammad Ali Khayamian, Tehran (IR); Mohammad Abdolahad, Tehran (IR); Hamed Abadijoo, Tehran (IR); Mahsa Faramarzpour Darzini, Tehran (IR); Mohammadreza Ghaderinia, Tehran (IR); Hossein Simaee, Tehran (IR); Seyed Mojtaba Yazdanparast, Tehran (IR); Shahriar Shalileh, Tehran (IR)

(73) Assignee: NANO HESGARSAZAN SALAMAT ARYA, Tehran (IR)

(*) Notice: Subject to any disclaimer, the term of this patent is extended or adjusted under 35 U.S.C. 154(b) by 5 days.

(21) Appl. No.: 17/698,846

(22) Filed: Mar. 18, 2022

(65) Prior Publication Data
US 2022/0202305 A1 Jun. 30, 2022

Related U.S. Application Data

(60) Provisional application No. 63/233,221, filed on Aug. 14, 2021.

(51) Int. Cl.
A61B 5/05 (2021.01)
A61B 5/053 (2021.01)
(Continued)

(52) U.S. Cl.
CPC .............. *A61B 5/053* (2013.01); *A61N 1/0404* (2013.01); *A61N 1/32* (2013.01); *A61N 1/40* (2013.01)

(58) Field of Classification Search
CPC .... A61N 1/0404; A61N 1/32; A61N 1/36034; A61N 1/40; A61B 5/053
See application file for complete search history.

(56) References Cited

U.S. PATENT DOCUMENTS 7,333,852 B2 * 2/2008 Palti ................. A61N 1/326
607/2
7,565,205 B2 * 7/2009 Palti ................. A61N 1/40
607/76

(Continued)

*Primary Examiner* — Amanda K Hulbert
(74) *Attorney, Agent, or Firm* — Bajwa IP Law Firm; Haris Zaheer Bajwa

(57) ABSTRACT

A method for preventing cytokine storm by suppressing clonal expansion of hyperactivated lymphocytes in a COVID-19 infected patient. The method includes placing at least four electrodes on skin of the COVID-19 infected patient by putting at least two electrodes at two locations over chest in front of ribcage of the COVID-19 infected patient and putting at least two other electrodes at two locations adjacent to lung tissue of the COVID-19 infected patient and suppressing mitosis of hyperactivated proliferative lymphocytes cells within the lung tissue of the COVID-19 infected patient by electrically stimulating the hyperactivated proliferative lymphocytes. Electrically stimulating the hyperactivated proliferative lymphocytes includes generating an alternating electric field (AEF) within the lung tissue by applying an AC voltage to the at least four electrodes and periodically changing a direction of the (Continued)

generated AEF in a plurality of directions within the lung tissue.

10 Claims, 26 Drawing Sheets

(51) Int. Cl.
*A61N 1/04* (2006.01)
*A61N 1/32* (2006.01)
*A61N 1/40* (2006.01)

(56) References Cited

U.S. PATENT DOCUMENTS

| | | | |
|---|---|---|---|
| 7,715,921 B2 * | 5/2010 | Palti | A61N 1/0408 |
| | | | 607/148 |
| RE43,618 E * | 8/2012 | Palti | A61N 1/326 |
| | | | 607/2 |
| 11,020,585 B2 * | 6/2021 | Alon | A61N 1/0456 |
| 11,529,511 B2 * | 12/2022 | Chang | A61F 7/007 |
| 2020/0016399 A1 * | 1/2020 | Kaynan | A61N 1/40 |
| 2021/0228895 A1 * | 7/2021 | Nicacio | A61N 1/40 |
| 2022/0088403 A1 * | 3/2022 | Voloshin-Sela | A61N 1/40 |

* cited by examiner

PREVENTING CYTOKINE STORM IN COVID-19 PATIENTS BY SUPPRESSING CLONAL EXPANSION IN ACTIVATED LYMPHOCYTES USING ALTERNATING ELECTRIC FIELDS

1302

1304

PREVENTING CYTOKINE STORM IN COVID-19 PATIENTS BY SUPPRESSING CLONAL EXPANSION IN ACTIVATED LYMPHOCYTES USING ALTERNATING ELECTRIC FIELDS

CROSS-REFERENCE TO RELATED APPLICATION

This application claims the benefit of priority from U.S. Provisional Patent Application Ser. No. 63/233,221 filed on Aug. 14, 2021, and entitled "PREVENTING CYTOKINE STORM IN COVID-19 PATIENTS BY SUPPRESSING CLONAL EXPANSION IN ACTIVATED LYMPHOCYTES USING ALTERNATING ELECTRIC FIELD", which is incorporated herein by reference in its entirety.

TECHNICAL FIELD

The present disclosure generally relates to anti-inflammation method for COVID-19 infected patients, and particularly, to a method for suppression of clonal expansion of highly activated and proliferative lymphocytes in COVID-19 infected patients and a consequent reduction in cytokines released by lymphocytes utilizing application of an alternating electric field (AEF) to a part of a patient's body infected with COVID-19 (e.g., lung tissue) with highly activated and proliferative lymphocytes therein.

BACKGROUND

More than 200 million infections with at least 4 million deaths worldwide is just a small part of the consequences that a 100 nm coronavirus has imposed on the world community since its emergence in 2019. After infection and commencement of the immunological phase of COVID-19 disease, many clinical manifestations may arise, but acute respiratory distress syndrome (ARDS) is one of the most lethal features of the COVID-19. Numerous pieces of evidence suggest that severity of COVID-19 infection and ARDS is highly correlated with the proinflammatory cytokine levels in bloodstream and an intensity of immune cell hyperactivation caused by the COVID-19 virus.

Out-of-control secretion of cytokine proteins with subsequent hyper-activation of immune system causes severe systemic damage to tissues and organs throughout an infected body, such as pulmonary dysfunction and renal failure. To prevent exacerbation and progression of coronavirus disease in such patients, a broad range of immunosuppressor drugs such as corticosteroids, JAK inhibitors, etc., are used as a general treatment. For instance, dexamethasone therapy has shown promising results in reducing severity of COVID-19 infection, suppressing cytokine storm, and consequent hyperinflammation phase of coronavirus disease. One major effect of the immunosuppressor drugs such as dexamethasone is their antiproliferative effect. In fact, dexamethasone impairs proliferation of lymphocytes such as T cells during their clonal expansion. Although many benefits are associated with administration of dexamethasone for suppression of severe inflammations, numerous negative serious side effects such as increased risk of sepsis, calcium metabolism, kidney disorders, etc., are also inevitable.

Hence, there is a need for a simple, fast, and cost-effective method, system, and associated apparatus for suppressing cytokine storm in patients who are infected with an inflammatory disease or a hyperactivation of immune system, such as COVID-19 patients. There is even a need for preventing cytokine storm in patients with hyperactivated immune system at early stage of their disease, specifically, in COVID-19 patients. There is also a need for method, system, and associated apparatus for preventing or suppressing cytokine storm in patients without causing any significant side effects.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for preventing cytokine storm by suppressing clonal expansion of hyperactivated lymphocytes in a COVID-19 infected patient. The method may include placing at least two electrodes on skin of a COVID-19 infected patient and suppressing mitosis of hyperactivated proliferative lymphocytes within lung tissue of the COVID-19 infected patient by electrically stimulating the hyperactivated proliferative lymphocytes.

In an exemplary implementation, placing the at least two electrodes on skin of the COVID-19 infected patient may include putting a first electrode of the at least two electrodes on skin of the COVID-19 infected patient at a location of a first portion of lung tissue of the COVID-19 infected patient and putting a second electrode of the at least two electrodes on skin of the COVID-19 infected patient at a location of a second portion of lung tissue of the COVID-19 infected patient.

In an exemplary implementation, electrically stimulating the hyperactivated proliferative lymphocytes may include connecting the at least two electrodes to an AC function generator device and generating an alternating electric field (AEF) within the lung tissue of the COVID-19 infected patient by applying an AC voltage between the at least two electrodes utilizing the AC function generator device.

In an exemplary implementation, placing the at least two electrodes on skin of the COVID-19 infected patient may include placing at least two electrically conductive elements on skin of the COVID-19 infected patient, where an area of each respective electrically conductive element may be in a range between 1 $cm^2$ and 100 $cm^2$. In an exemplary implementation, placing the at least two electrodes on skin of the COVID-19 infected patient may include placing at least two electrically conductive plates made of at least one of aluminum (Al), copper (Cu), stainless steel, gold (Au), chromium (Cr), Titanium (Ti), and combinations thereof on skin of the COVID-19 infected patient.

In an exemplary implementation, applying the AC voltage between the at least two electrodes may include applying an AC voltage in a range between 0.5 V/cm and 7 V/cm with a constant frequency in a range between 50 kHz and 200 kHz between the at least two electrodes.

In an exemplary implementation, suppressing mitosis of hyperactivated proliferative lymphocytes cells within the lung tissue of the COVID-19 infected patient by electrically stimulating the hyperactivated proliferative lymphocytes may be done for a pre-determined period of time. In an exemplary embodiment, the pre-determined period of time may include at least 20 hours including at least one of a continuous time interval, a plurality of intermittent time intervals, and combinations thereof.

In another general aspect, the method for preventing cytokine storm by suppressing clonal expansion of hyperactivated lymphocytes in a COVID-19 infected patient may include placing at least four electrodes on skin of a COVID-19 infected patient and suppressing mitosis of hyperactivated proliferative lymphocytes cells within lung tissue of the COVID-19 infected patient by electrically stimulating the hyperactivated proliferative lymphocytes.

In an exemplary implementation, placing the at least four electrodes on skin of the COVID-19 infected patient may include putting a first electrode and a second electrode of the at least four electrodes on skin of the COVID-19 infected patient at two respective locations over chest in front of ribcage of the COVID-19 infected patient and putting a third electrode and a fourth electrode of the at least four electrodes on skin of the COVID-19 infected patient at respective two locations maximally 10 cm apart from a central part of lung tissue of the COVID-19 infected patient.

In an exemplary implementation, electrically stimulating the hyperactivated proliferative lymphocytes may include connecting the at least four electrodes to an AC function generator device, generating an alternating electric field (AEF) within the lung tissue of the COVID-19 infected patient by applying an AC voltage to the at least four electrodes utilizing the AC function generator device, and stimulating the hyperactivated proliferative lymphocytes with mitotic spindle aligned in a plurality of directions by periodically changing a direction of the generated AEF in the plurality of directions within the lung tissue.

In an exemplary implementation, suppressing mitosis of hyperactivated proliferative lymphocytes cells within the lung tissue of the COVID-19 infected patient by electrically stimulating the hyperactivated proliferative lymphocytes may be done for a pre-determined period of time. In an exemplary embodiment, the pre-determined period of time may include at least 20 hours in form of at least one of a continuous time interval, a plurality of intermittent time intervals, and combinations thereof.

In an exemplary implementation, periodically changing the direction of the generated AEF in the plurality of directions within the lung tissue may include periodically switching of signal poles and ground poles of the applied AC voltage between at least two respective electrodes of the at least four electrodes at each time step of the pre-determined period of time. In an exemplary implementation, each time step of the pre-determined period of time may include a time interval between 0.5 second and 5 seconds of the pre-determined period of time.

In an exemplary implementation, placing the at least four electrodes on skin of the COVID-19 infected patient may include placing at least four electrically conductive elements on skin of the COVID-19 infected patient, where an area of each respective electrically conductive element may be in a range between 1 cm² and 100 cm². In an exemplary implementation, placing the at least four electrodes on skin of the COVID-19 infected patient may include placing at least two electrically conductive plates made of at least one of aluminum (Al), copper (Cu), stainless steel, gold (Au), chromium (Cr), Titanium (Ti), and combinations thereof on skin of the COVID-19 infected patient.

In an exemplary implementation, applying the AC voltage to the at least four electrodes may include applying an AC voltage in a range between 0.5 V/cm and 7 V/cm with a constant frequency in a range between 50 kHz and 200 kHz to the at least four electrodes.

In an exemplary implementation, putting the at least two electrodes on skin of the COVID-19 infected patient at the respective two locations maximally 10 cm apart from the central part of the lung tissue of the COVID-19 infected patient may include putting the at least two electrodes at respective two locations of skin place over at least one of chest, armpit, waist, shoulder, back and combinations thereof of the COVID-19 infected patient.

In another general aspect of the present disclosure, a method for preventing cytokine storm by suppressing clonal expansion of hyperactivated lymphocytes in a patient infected by an inflammatory disease is described. The method may include placing at least four electrodes on skin of a patient infected by an inflammatory disease and suppressing mitosis of hyperactivated proliferative lymphocytes cells within the infected organ by electrically stimulating the hyperactivated proliferative lymphocytes therein.

In an exemplary implementation, placing the at least four electrodes on skin of the patient infected by the inflammatory disease may include putting the at least four electrodes over skin of the patient at respective four locations maximally 10 cm apart from a central part of an infected organ of the patient. In an exemplary embodiment, the infected organ of the patient may include a plurality of hyperactivated lymphocytes therein.

In an exemplary implementation, suppressing mitosis of the hyperactivated proliferative lymphocytes cells within the infected organ by electrically stimulating the hyperactivated proliferative lymphocytes therein may include connecting the at least four electrodes to an AC function generator device, generating an alternating electric field (AEF) within the infected organ by applying an AC voltage to the at least four electrodes utilizing the AC function generator device, and stimulating the hyperactivated proliferative lymphocytes with mitotic spindle aligned in a plurality of directions by periodically changing a direction of the generated AEF in the plurality of directions within the infected organ.

In an exemplary implementation, suppressing mitosis of the hyperactivated proliferative lymphocytes cells within the infected organ by electrically stimulating the hyperactivated proliferative lymphocytes may be done for a pre-determined period of time, where the pre-determined period of time may include at least 20 hours in form of at least one of a continuous time interval and a plurality of intermittent time intervals.

In an exemplary implementation, periodically changing the direction of the generated AEF in the plurality of directions within the infected organ may include periodically switching of signal poles and ground poles of the applied AC voltage between at least two respective electrodes of the at least four electrodes at each time step of the pre-determined period of time. In an exemplary implementation, each time step of the pre-determined period of time may include a time interval between 0.5 second and 5 seconds of the pre-determined period of time.

In an exemplary implementation, placing the at least four electrodes on skin of the patient infected by the inflammatory disease may include placing at least four electrically conductive elements on skin of the patient infected by the inflammatory disease, where an area of each respective electrically conductive element may be in a range between 1 cm² and 100 cm². In an exemplary implementation, placing the at least four electrodes on skin of the patient infected by the inflammatory disease may include placing at least two electrically conductive plates made of at least one of aluminum (Al), copper (Cu), stainless steel, gold (Au), chromium (Cr), Titanium (Ti), and combinations thereof on skin of the patient.

In an exemplary implementation, applying the AC voltage to the at least four electrodes may include applying an AC voltage in a range between 0.5 V/cm and 7 V/cm with a constant frequency in a range between 50 kHz and 200 kHz to the at least four electrodes.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
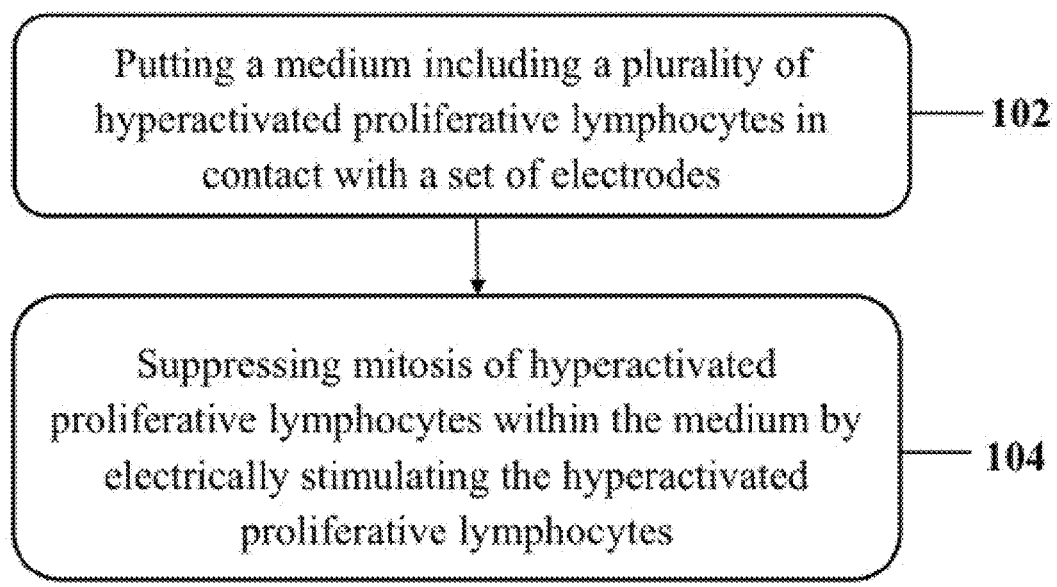
FIG. 1A shows an exemplary method for suppressing clonal expansion of hyperactivated lymphocytes, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Cytokines, which are signal proteins and mediators of an immune response to an inflammation, are secreted by a variety of cells, including lymphocytes, granulocytes, macrophages, endothelial cells, fibroblasts, etc., among which T cell lymphocytes are the dominant agents that level up released cytokines in bloodstream. A major reason of cytokine secretion by lymphocytes is attributed to their clonal expansion, a phenomenon by which activated lymphocytes produce more of themselves through mitosis division with the same antigen against a specific pathogen. Hence, controlling such mitosis would be of interest in suppression of immune hyperactivation in patients infected by an inflammatory disease, such as COVID-19 patients.

But, all medical procedures for the treatment of COVID-19 infection, up to now, are just limited to chemical drugs. All of scientists believe that a major challenge impacting mortality of COVID-19 patients is an out-of-control immune system activation and a subsequent cytokine production. During this process, adaptive an exemplary immune system is highly activated, and many of lymphocytes start to clonally expand, and hence many cytokines are also released. So, any ability to harness this cytokine storm and calm down an immune outrage is helpful. While the most infected battleground for immune hyperactivation in COVID-19 infected patients is their lung tissue, the only medical treatment for suppression of hypercytokinemia is based on immunosuppressor drugs that systemically dampen immunity with many unavoidable negative side effects such as increasing risk of sepsis, calcium metabolism, kidney disorders, etc.

Herein, an in-vitro and an in-vivo implementation of a method for suppressing clonal expansion of highly activated and proliferative lymphocytes is described. An exemplary method may include applying an alternating electric field (AEF) to highly activated and proliferative lymphocytes; thereby, resulting in electrically stimulating highly activated and proliferative lymphocytes leading to reducing mitosis division of such lymphocytes and consequently, reducing cytokine production by such lymphocytes. Herein, "highly activated (hyperactivated) lymphocytes and/or highly proliferative lymphocytes" may refer to lymphocytes of an exemplary immune system of a patient infected with an inflammatory diseases, such as COVID-19. Exemplary hyperactivated lymphocytes may be highly proliferative and divide rapidly, so a number of lymphocytes may rapidly increase in an infected organ or tissue. Furthermore, hyperactivated lymphocytes may release large amounts of cytokines in an infected organ or tissue; thereby, resulting in a cytokine storm there. Lymphocyte activation/hyperactivation occurs when lymphocytes (B cells or T cells) are triggered through antigen-specific receptors on their cell surface. This causes the B cells or T cells to proliferate and differentiate into specialized effector lymphocytes. An exemplary method for suppressing clonal expansion of highly activated and proliferative lymphocytes may include exposing a medium, organ, or tissue within a patient's body to an AEF, where the medium, organ, or tissue within the patient's body may include a plurality of highly activated and proliferative lymphocytes caused by an inflammatory disease, such as COVID-19 infection.

Herein, an exemplary method, system, and apparatus is described for preventing and/or suppressing cytokine storm in a patient's body. An exemplary method, system, and apparatus may be utilized for locally preventing and/or suppressing cytokine storm in a target location of patient's body involved with a hyperactivation of immune system there. In an exemplary embodiment, an exemplary method, system, and apparatus may be utilized to suppress clonal expansion of highly activated and proliferative lymphocytes and consequently, reduce cytokines releasing by lymphocytes. An exemplary method may include electrically stimulation of highly expanding lymphocytes by an alternating electric field (AEF) during a hyperactivation of an immune system caused by an inflammation, such as COVID-19 infection. An exemplary method may include applying AEF to a target location of highly expanding lymphocytes, for example, lung of a COVID-19 infected patient by delivering low intensity and intermediate frequency electric field to the target location. An exemplary applied AEF may disrupt mitotic spindle assembly of highly dividing cells so that abnormally dividing cells with prolonged mitosis phase (during their cell cycle) undergo apoptosis. Since applying AEF may have an antimitotic mechanism, the most affected cells may include highly proliferative ones, such as highly expanding lymphocytes, while healthy cells with a low rate of division may not be damaged during such electrical stimulation. In an antimitotic mechanism, AEF may exert directional forces on polar microtubules and interfere with assembly of normal mitotic spindle. Such interference with microtubule dynamics may result in abnormal spindle formation and subsequent mitotic arrest or delay. Since mitosis may not occur for lymphocytes that are not activated, therefore, healthy cells may remain immune from AEF effect.

On this basis, AEF may be safely applied for each patient to suppress highly activated and expanding lymphocytes and consequently reducing an amount of released cytokines into bloodstream. Currently, suppression of cytokine storm in COVID-19 infected patients is implemented using systemic administration of immunosuppressor drugs that debilitate entire immune system. Whereas, AEF stimulation consistent with exemplary embodiments may be applied locally to an organ affected by COVID-19 virus, i.e., lung tissue without any effect on the other immune cells by impacting only highly expanding lymphocytes in a target highly infected organ, e.g., lung tissue.

In an exemplary implementation, an exemplary method for suppressing clonal expansion of hyperactivated lymphocytes is described. FIG. 1A shows exemplary method 100 for suppressing clonal expansion of hyperactivated lymphocytes, consistent with one or more exemplary embodiments of the present disclosure. Exemplary method 100 may include putting a medium including a plurality of hyperactivated proliferative lymphocytes in contact with a set of electrodes (step 102) and suppressing mitosis of hyperactivated proliferative lymphocytes within the medium by electrically stimulating the plurality of hyperactivated proliferative lymphocytes within the medium (step 104).

Figure 1B:
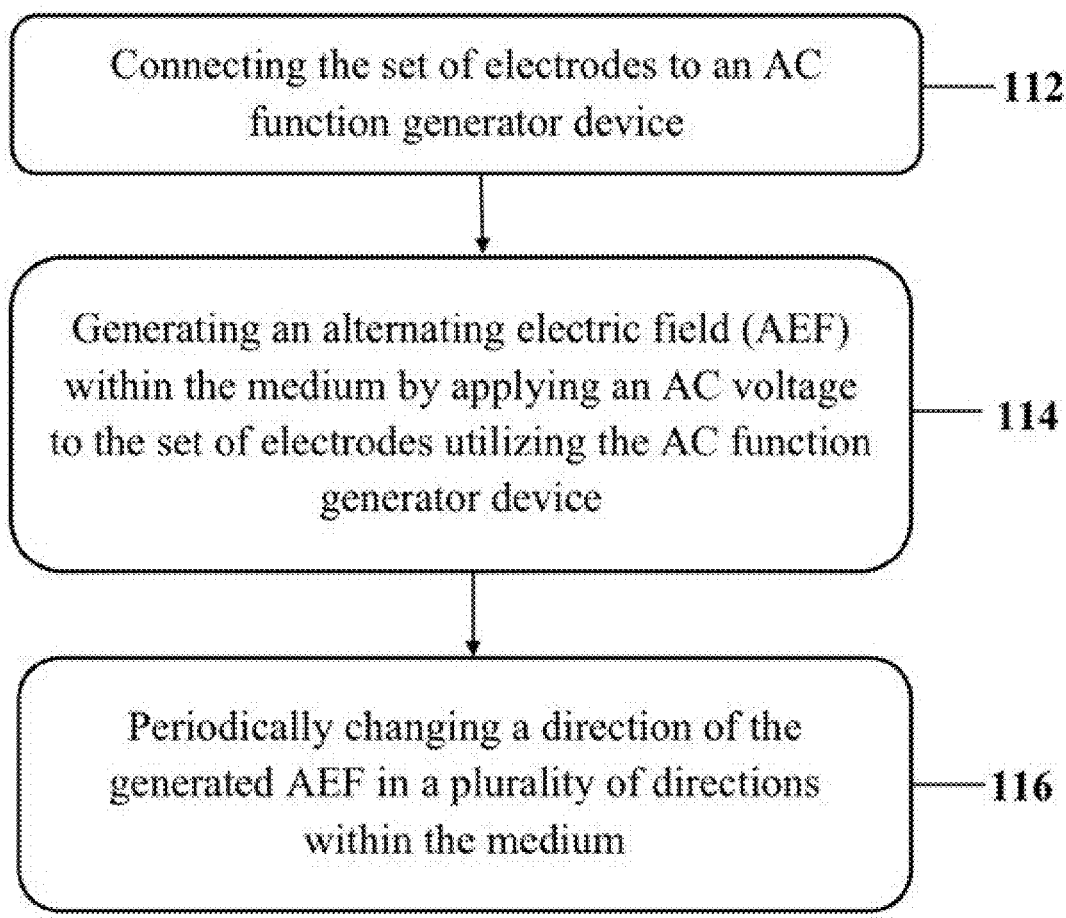
FIG. 1B shows an exemplary implementation of electrically stimulating a plurality of hyperactivated proliferative lymphocytes within an exemplary medium, consistent with one or more exemplary embodiments of the present disclosure.

FIG. 1B shows an exemplary implementation of electrically stimulating a plurality of hyperactivated proliferative lymphocytes within an exemplary medium (step 104), consistent with one or more exemplary embodiments of the present disclosure. In an exemplary implementation, electrically stimulating a plurality of hyperactivated proliferative lymphocytes within an exemplary medium (step 104) may include connecting an exemplary set of electrodes in contact with a medium containing a plurality of hyperactivated proliferative lymphocytes to an AC function generator device (step 112), generating an alternating electric field (AEF) within the medium by applying an AC voltage to the set of electrodes utilizing the AC function generator device (step 114), and stimulating the hyperactivated proliferative lymphocytes with respective mitotic spindles aligned in a plurality of directions by periodically changing a direction of the generated AEF in a plurality of directions within the medium (step 116).

In an exemplary implementation, exemplary method 100 may be conducted in-vitro for suppressing clonal expansion of hyperactivated lymphocytes in a biological sample as an exemplary medium including a plurality of hyperactivated proliferative lymphocytes. In an exemplary embodiment, the biological sample may include a sample of a bloodstream drawn from a patient involved with an inflammatory disease, such as COVID-19 infection. In an exemplary embodiment, the inflammatory disease may include a chronic inflammatory disease (CID). In an exemplary embodiment, the CID may include at least one of COVID-19 disease, SARS-CoV-2 infection, Flu, Sepsis, Auto inflammatory diseases, Graft versus host disease (GvHD), and combinations thereof.

In an exemplary in-vitro implementation of exemplary method 100, an exemplary biochip may be fabricated and used for conducting exemplary method 100 in-vitro. In an exemplary embodiment, an exemplary biochip may include a plurality of electrodes patterned and fabricated on a substrate. In an exemplary embodiment, the plurality of electrodes may be configured to allow to place a biological sample including a plurality of hyperactivated lymphocytes thereon and generate an AEF across one or more directions within a space among the plurality electrode. In an exemplary implementation, generating an AEF within an exemplary space among the plurality electrodes may include generating an AEF within the biological sample placed on the plurality of electrodes by applying an AC voltage to the plurality of electrodes utilizing an AC function generator device and suppressing clonal expansion of the plurality of hyperactivated lymphocytes responsive to an abnormal mitosis of the plurality of hyperactivated lymphocytes due to electrically stimulation of the plurality of hyperactivated lymphocytes by the generated AEF.

Figure 2:
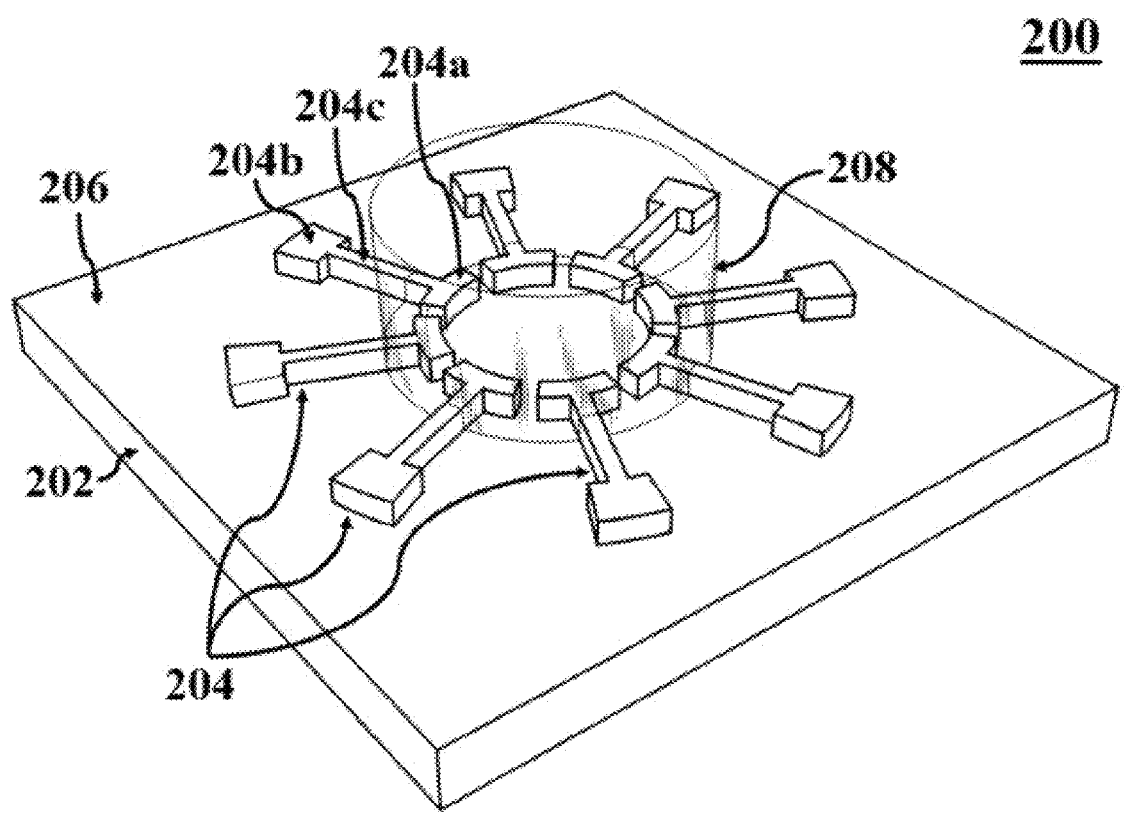
FIG. 2 shows a schematic view of an exemplary biochip for applying an alternating electric field (AEF) to a plurality of hyperactivated lymphocytes in a biological sample, consistent with one or more exemplary embodiments of the present disclosure.

FIG. 2 shows a schematic view of an exemplary biochip 200 for applying an alternating electric field (AEF) to a plurality of hyperactivated lymphocytes in a biological sample, consistent with one or more exemplary embodiments of the present disclosure. In an exemplary embodiment, biochip 200 may include exemplary substrate 202 and a set of electrodes 204. In an exemplary embodiment, each exemplary electrode of set of electrodes 204 may include respective electrode head 204a and respective electrode tail 204b. In an exemplary embodiment, exemplary electrode head 204a may include a respective distal end of an exemplary electrode of set of electrodes 204. In an exemplary embodiment, exemplary electrode tail 204b may include a respective proximal end of an exemplary electrode of set of electrodes 204. In an exemplary embodiment, each respective electrode of set of electrodes 204 may further include a respective middle part 204c between respective electrode head 204a and respective electrode tail 204b.

In an exemplary embodiment, a respective set of electrode heads 204a of set of electrodes 204 may be arranged in a symmetric circular pattern. In an exemplary symmetric circular pattern, set of electrodes 204 may include 8 electrodes, where each respective electrode head 204a may form a 400 secant of an exemplary symmetric circular pattern so that a distance of a 5° secant may be between each two electrode heads allowing for preventing a contact between two or more respective electrodes of set of electrodes 204. In an exemplary embodiment, exemplary symmetric circular pattern may have a radius of 5 mm. In an exemplary embodiment, each respective electrode tail 204b may include a 2 mm×2 mm square surface. Each respective electrode tail 204b may serve as a pad allowing for connecting each respective electrode of set of electrodes 204 to an exemplary AC function generator. In an exemplary embodiment, set of electrodes 204 may be made of gold. Due to an enormous electrical conductivity of gold, a length of middle part 204c between electrode head 204a and electrode tail 204b may not have a sensible effect on an applied AEF to set of electrodes 204. In an exemplary embodiment, a thickness of each electrode of set of electrodes 204 may be about 100 nm.

In an exemplary embodiment, electrode head 204a may be configured to be put in contact with a biological sample, for example, a medium including a plurality of hyperactivated proliferative lymphocytes (e.g., a blood sample drawn from a COVID-19 infected person). In an exemplary embodiment, an arrangement of set of electrodes 204 shown in FIG. 2 may include a circular arrangement of a respective set of electrode heads of set of electrodes 204. In an exemplary embodiment, an exemplary circular arrangement of respective set of electrode heads of set of electrodes 204 may form a circular space. In an exemplary embodiment, an exemplary circular space may be configured to put an exemplary biological sample thereon so that an exemplary biological sample may be in contact with respective set of electrode heads of set of electrodes 204.

In an exemplary embodiment, biochip 200 may further include exemplary liquid holder 208. In an exemplary embodiment, liquid holder 208 may be configured to hold a sample, such as the biological sample may be placed there inside on surface of electrode heads of set of electrodes 204. In an exemplary embodiment, liquid holder 208 may be placed around an exemplary circular space formed by an exemplary circular arrangement of respective set of electrode heads of set of electrodes 204. In an exemplary embodiment, set of electrodes 204 may be configured to allow an exemplary biological sample being placed thereon inside liquid holder 208 within an exemplary circular space. In an exemplary embodiment, liquid holder 208 may be placed around respective set of electrode heads 204*a* of set of electrodes 204 on surface 206 of substrate 202.

In an exemplary embodiment, electrode tail 204*b* may be configured to be connected to an electrical device, for example, an AC function generator device. In an exemplary embodiment, an exemplary AC function generator device may include an AC power supply for AC circuits. In an exemplary embodiment, an exemplary AC function generator device may be configured to provide a variable voltage source (or amplitude) as well as be able to vary a frequency magnitude or cycles per second. In an exemplary embodiment, an exemplary AC function generator device may include an electrical waveform generation circuit that produce electrical waveforms in different shapes (sine, saw tooth, triangular, square, etc.) with different voltage ranges and frequencies ranges. In an exemplary embodiment, an exemplary AC function generator device may include the transistor-based electronic circuits allowing for producing a desired waveform. In an exemplary embodiment, the AC function generator device may produce a potential difference between two or more electrically conductive elements connected to the AC function generator device by applying an electrical voltage to two or more electrically conductive elements. In an exemplary embodiment, an exemplary AC function generator device may be configured to generate different patterns of voltage signals over 2 or more electrodes. In an exemplary embodiment, an exemplary AC function generator device may be configured to apply an electrical voltage to set of electrodes 204 via respective electrode tails 204*b* connected to the AC function generator device.

In an exemplary embodiment, each exemplary electrode of set of electrodes 204 may be made of a biocompatible electrical conductive material. In an exemplary embodiment, each exemplary electrode of set of electrodes 204 may be made of at least one of aluminum (Al), copper (Cu), stainless steel, gold (Au), chromium (Cr), Titanium (Ti), and combinations thereof. In an exemplary embodiment, substrate 202 may include an electrically insulating material, for example, a glass slide. In an exemplary embodiment, substrate 202 may be made of at least one of glass, poly (methyl methacrylate) (PMMA), Polycarbonate, and combinations thereof. In an exemplary embodiment, set of electrodes 204 may be patterned and adhered on surface 206 of substrate 202.

In an exemplary implementation of exemplary method 100, biochip 200 may be utilized for suppressing clonal expansion of hyperactivated lymphocytes in-vitro. In an exemplary implementation, step 102 may include putting a medium including a plurality of hyperactivated proliferative lymphocytes in contact with set of electrodes 204. In an exemplary implementation, putting a medium including a plurality of hyperactivated proliferative lymphocytes in contact with set of electrodes 204 may include placing a biological sample including a plurality of hyperactivated proliferative lymphocytes on electrode heads of set of electrodes 204. In an exemplary implementation, placing an exemplary biological sample on electrode heads of set of electrodes 204 may include placing or dropping a blood sample inside liquid holder 208.

In an exemplary implementation, step 104 may include suppressing mitosis of hyperactivated proliferative lymphocytes within an exemplary medium being placed inside liquid holder 208 on electrode heads of set of electrodes 204. In an exemplary implementation, suppressing mitosis of hyperactivated proliferative lymphocytes within an exemplary medium may be done by electrically stimulating the plurality of hyperactivated proliferative lymphocytes within the medium. In an exemplary implementation, electrically stimulating the plurality of hyperactivated proliferative lymphocytes within an exemplary medium being placed inside liquid holder 208 on electrode heads of set of electrodes 204 (step 104) may include connecting set of electrodes 204 being in contact with an exemplary medium containing a plurality of hyperactivated proliferative lymphocytes to an AC function generator device (step 112), generating an AEF within an exemplary medium being placed on electrode heads of set of electrodes 204 by applying an AC voltage to set of electrodes 204 utilizing the AC function generator device (step 114).

In an exemplary implementation, connecting set of electrodes 204 being in contact with an exemplary medium containing a plurality of hyperactivated proliferative lymphocytes to an AC function generator device (step 112) may include connecting a respective set of electrode tails of set of electrodes 204 to a set of outputs of an exemplary AC function generator device. In an exemplary embodiment, set of electrodes 204 may include an even number of electrodes, including a plurality of electrode pairs, where each electrode pair of set of electrodes 204 may be configured to be connected to a respective signal output and a respective ground output of an exemplary AC function generator device. Thereby, an AEF field may be generated between electrodes of each electrode pair by applying an AC voltage between two electrodes of each electrode pair utilizing the AC function generator device. In an exemplary implementation, the generated AEF may exert force on alpha and beta tubulin heterodimers during formation of mitotic spindle while cell division of hyperactivated proliferative lymphocytes is being done. An exemplary exerted force may disrupt mitotic spindle and dividing cells may undergo apoptosis; thereby, a suppression in mitosis of hyperactivated proliferative lymphocytes may occur.

In an exemplary implementation, generating an AEF within an exemplary medium being placed on electrode heads of set of electrodes 204 (step 114) may include applying an AC voltage to set of electrodes 204 utilizing the AC function generator device. In an exemplary embodiment, applying the AC voltage to set of electrodes 204 utilizing the AC function generator device may include applying the AC voltage between two subsets of set of electrodes 204 utilizing the AC function generator device. In an exemplary embodiment, two subsets of set of electrodes 204 may include a first subset of set of electrodes 204 and a second subset of set of electrodes 204. In an exemplary embodiment, the first subset of electrodes 204 and the second subset of electrodes 204 may include an equal number of electrodes from set of electrodes 204. In an exemplary embodiment, the first subset of electrodes 204 may include half of electrodes of exemplary set of electrodes 204, and the first subset of electrodes 204 may be configured to be connected to signal output of an exemplary AC function generator device. Furthermore, the second subset of electrodes 204 may include the other half of electrodes of exemplary set of electrodes 204, and the second subset of electrodes 204 may be configured to be connected to ground output of an exemplary AC function generator device allowing for applying the AC voltage between the first subset of electrodes 204 and the second subset of electrodes 204. In an exemplary embodiment, electrodes of the first subset of electrodes 204 and the second subset of electrodes 204 may not be in a specific or pre-determined order and may alternate during applying the AC voltage by replacing one electrode of the first subset of electrodes 204 connected to an exemplary signal output by another one electrode of the second subset of electrodes 204 connected to an exemplary ground output. In an exemplary embodiment, electrodes of the first subset of electrodes 204 may include half of electrodes of exemplary set of electrodes 204 placed next to each other, and electrodes of the second subset of electrodes 204 may include the other half of electrodes of exemplary set of electrodes 204 also placed next to each other.

In an exemplary implementation, applying an AC voltage to set of electrodes 204 utilizing the AC function generator device may include applying an AC voltage in a range between 0.5 V/cm and 7 V/cm with a constant frequency in a range between 50 kHz and 200 kHz to set of electrodes 204 utilizing the AC function generator device. In an exemplary implementation, applying an AC voltage to set of electrodes 204 utilizing the AC function generator device may include applying an AC voltage of 3 V/cm with a constant frequency of 100 kHz to set of electrodes 204 utilizing the AC function generator device.

In an exemplary implementation, electrically stimulating an exemplary plurality of hyperactivated proliferative lymphocytes within an exemplary medium being placed inside liquid holder 208 on electrode heads of set of electrodes 204 (step 104) may further include stimulating the hyperactivated proliferative lymphocytes with respective mitotic spindles aligned in a plurality of directions by periodically changing a direction of the generated AEF in a plurality of directions within the medium (step 116). It should be noted that in process of cell mitosis, for example, in mitosis of lymphocytes, an orientation of a mitotic spindle may determine a plane of cell division. Spindle orientation of cells appears to be a consequence of cell elongation along a zero-force direction. In a state of no external force applied to cells, cells may have mitotic spindles aligned to various directions, where by applying an external force to cells, cells may align their mitotic spindle perpendicular to the external force. So, applying an external force to cells, for example, applying an electrical field (e.g., AEF) to cells, may lead to arrange mitotic spindles of cells in directions dictated by the external force. It should be noted that the applied AEF may affect highly activated lymphocytes only if a direction of the applied AEF is aligned with a mitotic spindle of lymphocytes being divided. In an exemplary embodiment, a direction of the applied may be changed periodically leading to increase a probability of alignment of the applied AEF direction with a direction of lymphocytes' mitotic spindle. In an exemplary implementation, periodically changing a direction of the generated AEF in a plurality of directions within the medium may include changing a direction of the generated AEF by an amount of degrees, for example, 45 degrees (45°) clockwise or counterclockwise per each time step of a set of time steps, for example, per second.

Figure 3A:
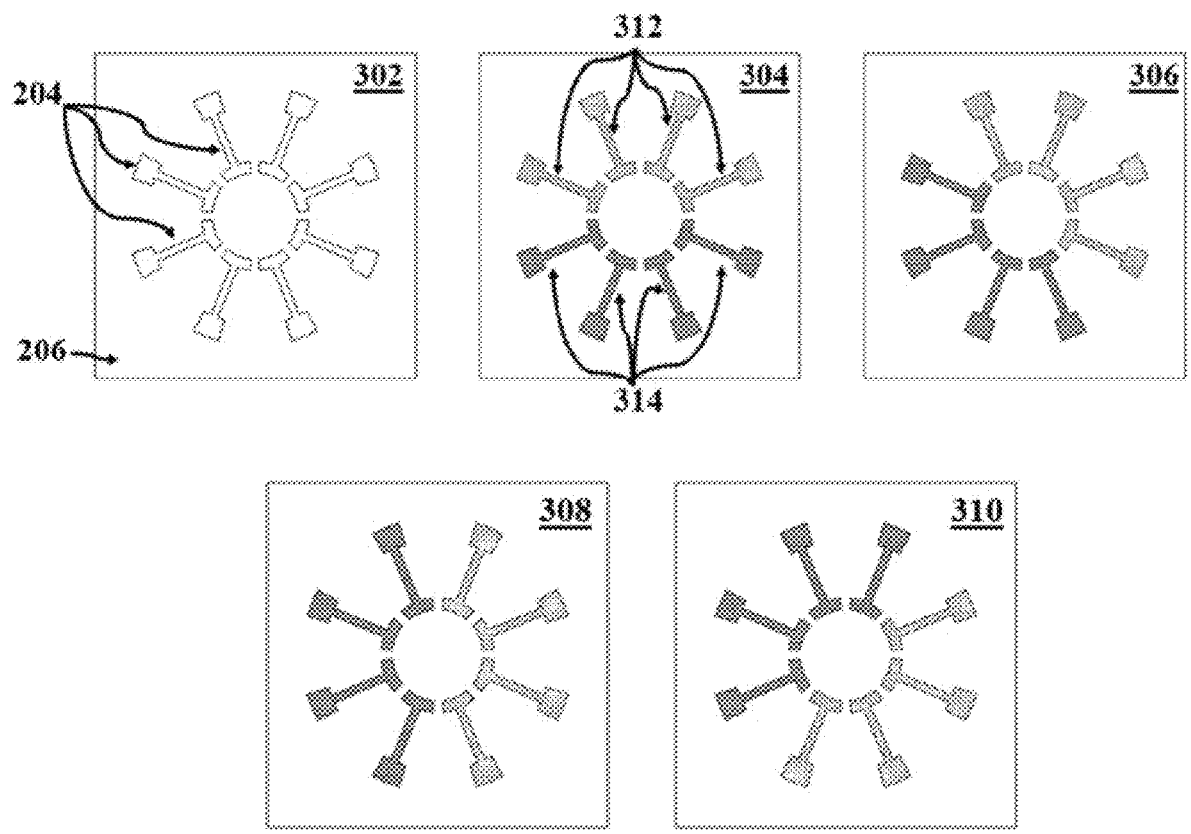
FIG. 3A shows a series of schematic top views of electrodes arrangements of an exemplary biochip in different scenarios including while applying no electric field and while applying AEF in various directions to a plurality of hyperactivated lymphocytes in an exemplary biological sample placed on electrode heads of an exemplary set of electrodes, consistent with one or more exemplary embodiments of the present disclosure.

FIG. 3A shows a series of schematic top views 302-312 of electrodes arrangement of an exemplary biochip 200 in different exemplary scenarios while applying no electric field (schematic view 302) and while applying AEF in various directions (schematic views 304-310) to a plurality of hyperactivated lymphocytes in an exemplary biological sample placed on electrode heads of set of electrodes 204, consistent with one or more exemplary embodiments of the present disclosure. In an exemplary embodiment, set of electrodes 204 may include two subsets of electrodes, including a first subset of electrodes 312 (designated by a dotted pattern) and a second subset of electrodes 314 (designated by a diagonal pattern). In an exemplary implementation, step 114 may include applying an AC voltage between first subset of electrodes 312 and second subset of electrodes 314 utilizing the AC function generator device. In an exemplary implementation, electrode tails of first subset of electrodes 312 may be connected to signal output port(s) of the AC function generator device and electrode tails of second subset of electrodes 314 may be connected to ground output port(s) of the AC function generator device so that two poles may be formed. In an exemplary embodiment, the formed two poles may include two subsets 312 and 314 of electrodes with a face-to-face array and in a symmetrical pattern.

In an exemplary implementation, periodically changing a direction of the generated AEF in a plurality of directions within the medium (step 116) may include periodically changing arrangement of electrodes of first subset of electrodes 312 and second subset of electrodes 314 as shown in exemplary arrangements 304-310. In an exemplary implementation, periodically changing a direction of the generated AEF in a plurality of directions within the medium (step 116) may include periodically changing electrodes of first subset of electrodes 312 and second subset of electrodes 314 by replacing at least one electrode of first subset of electrodes 312 with at least one electrode of second subset of electrodes 314; thereby, resulting in forming various arrangements of electrodes of first subset of electrodes 312 and second subset of electrodes 314.

Figure 3B:
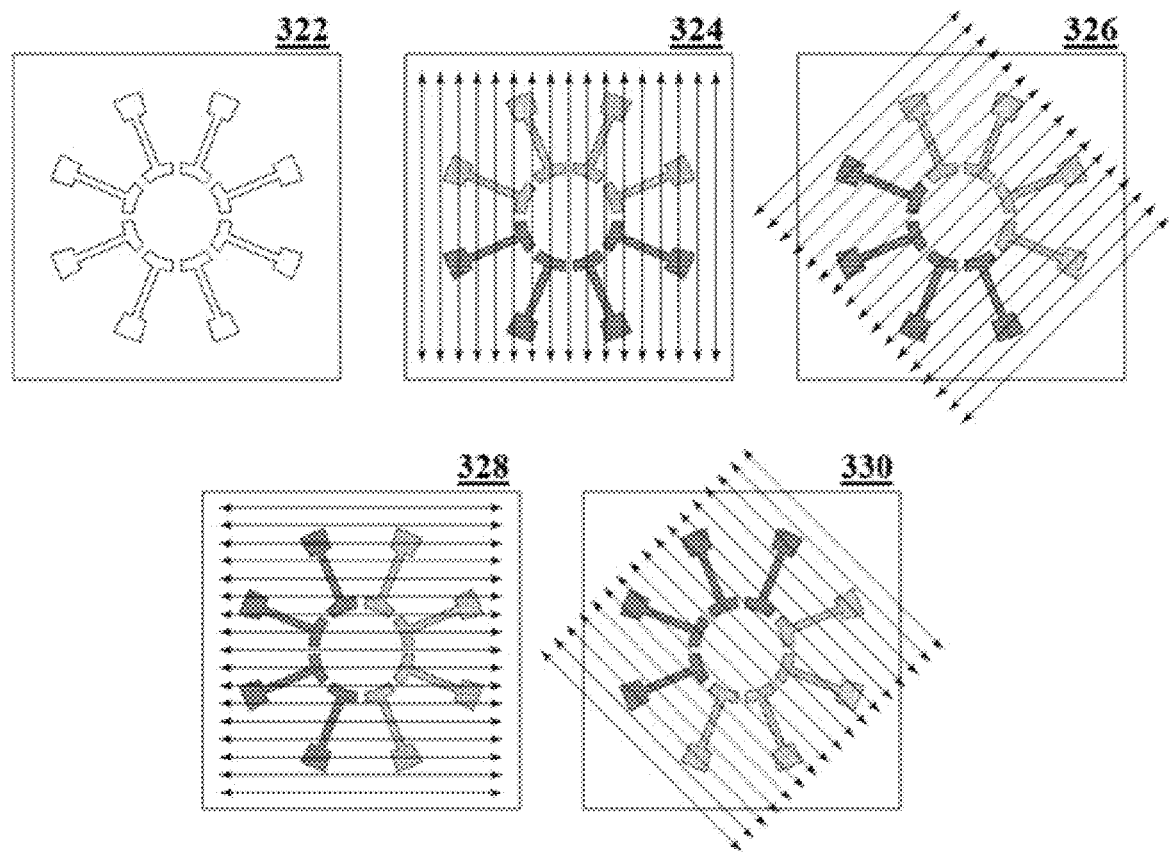
FIG. 3B shows a series of schematic top views of directions of exemplary generated AEF on an exemplary biochip in different scenarios including while applying no electric field and while applying AEF in various directions to a plurality of hyperactivated lymphocytes in an exemplary biological sample placed on electrode heads of an exemplary set of electrodes, consistent with one or more exemplary embodiments of the present disclosure.

In an exemplary implementation, periodically changing a direction of the generated AEF in a plurality of directions within the medium (step 116) may further include applying AEF in various directions by applying an electrical voltage between first subset of electrodes 312 and second subset of electrodes 314 with various formed arrangements. FIG. 3B shows a series of schematic top views 322-330 of directions of exemplary generated AEF on an exemplary biochip 200 in different scenarios including while applying no electric field (schematic view 322) and while applying AEF in various directions (schematic views 324-330) to a plurality of hyperactivated lymphocytes in an exemplary biological sample placed on electrode heads of set of electrodes 204, consistent with one or more exemplary embodiments of the present disclosure. As shown in FIG. 3B, periodically changing a direction of the generated AEF in a plurality of directions within the medium may include changing a direction of the generated AEF by 45 degrees (45°) clockwise per second.

It should be noted that cells may have mitotic spindles in various alignments. So, changing an AEF generated direction periodically in various cycles (e.g., cycles 324-330)

may lead to increase a chance of parallelism between the AEF direction and an axis of cell division. Referring to FIGS. 3A and 3B, by switching from one arrangement of electrodes to another, for example, from arrangement 304 to arrangement 306, a direction of the applied AEF may be changed from direction 324 to direction 326. Accordingly, the applied AEF may sweep a range of cycles of directions and a uniform electric field distribution inside the medium containing clusters of activated and expanding lymphocytes may be generated that may lead to impact all of expanding cells with different spindle alignments. In each cycle, mitotic arrest induced by the generated AEF may occur for cells whose mitotic spindle is aligned in a direction of the applied electric field, while cells with unaligned spindle may be affected in another cycle.

In an exemplary implementation, periodically changing a direction of the generated AEF in a plurality of directions within the medium (step 116) may include periodically switching a direction of the generated AEF from a direction to another every time interval. In an exemplary implementation, periodically changing a direction of the generated AEF in a plurality of directions within the medium (step 116) may include periodically switching a direction of the generated AEF from a direction to another every second. In an exemplary implementation, each cycle of electrodes arrangement may last for about one second.

In an exemplary implementation, exemplary method 100 may be conducted in-vivo for suppressing clonal expansion of hyperactivated lymphocytes in a patient. In an exemplary implementation, exemplary method 100 may be conducted in-vivo for suppressing clonal expansion of hyperactivated lymphocytes in a patient infected by an inflammatory disease, such as COVID-19 infection. In an exemplary embodiment, the inflammatory disease may include at least one of a chronic inflammatory disease (CID), COVID-19 disease, SARS-CoV-2 infection, Flu, Sepsis, Auto inflammatory diseases, Graft versus host disease (GvHD), and combinations thereof. Referring to FIG. 1A, exemplary method 100 may include putting a medium including a plurality of hyperactivated proliferative lymphocytes in contact with a set of electrodes (step 102) and suppressing mitosis of hyperactivated proliferative lymphocytes within the medium by electrically stimulating the plurality of hyperactivated proliferative lymphocytes within the medium (step 104).

In an exemplary implementation, putting a medium including a plurality of hyperactivated proliferative lymphocytes in contact with a set of electrodes (step 102) may include putting an infected organ or tissue of a patient infected by an inflammatory disease in contact with a set of electrodes. In an exemplary embodiment, the infected organ may include at least one of heart, lung, kidney, etc. In an exemplary implementation, putting an infected organ or tissue of a patient infected by an inflammatory disease in contact with a set of electrodes may include putting lung tissue of a COVID-19 infected patient in contact with a set of electrodes. In an exemplary implementation, putting a medium including a plurality of hyperactivated proliferative lymphocytes in contact with a set of electrodes (step 102) may include placing a set of electrodes on skin of a patient infected by an inflammatory disease.

In an exemplary embodiment, the set of electrodes may include electrically conductive elements with an area of each respective electrically conductive element in a range between about 1 cm$^2$ and about 100 cm$^2$. In an exemplary embodiment, the set of electrodes may include electrically conductive elements made of at least one of aluminum (Al), copper (Cu), stainless steel, gold (Au), chromium (Cr), Titanium (Ti), and combinations thereof.

Figure 4A:
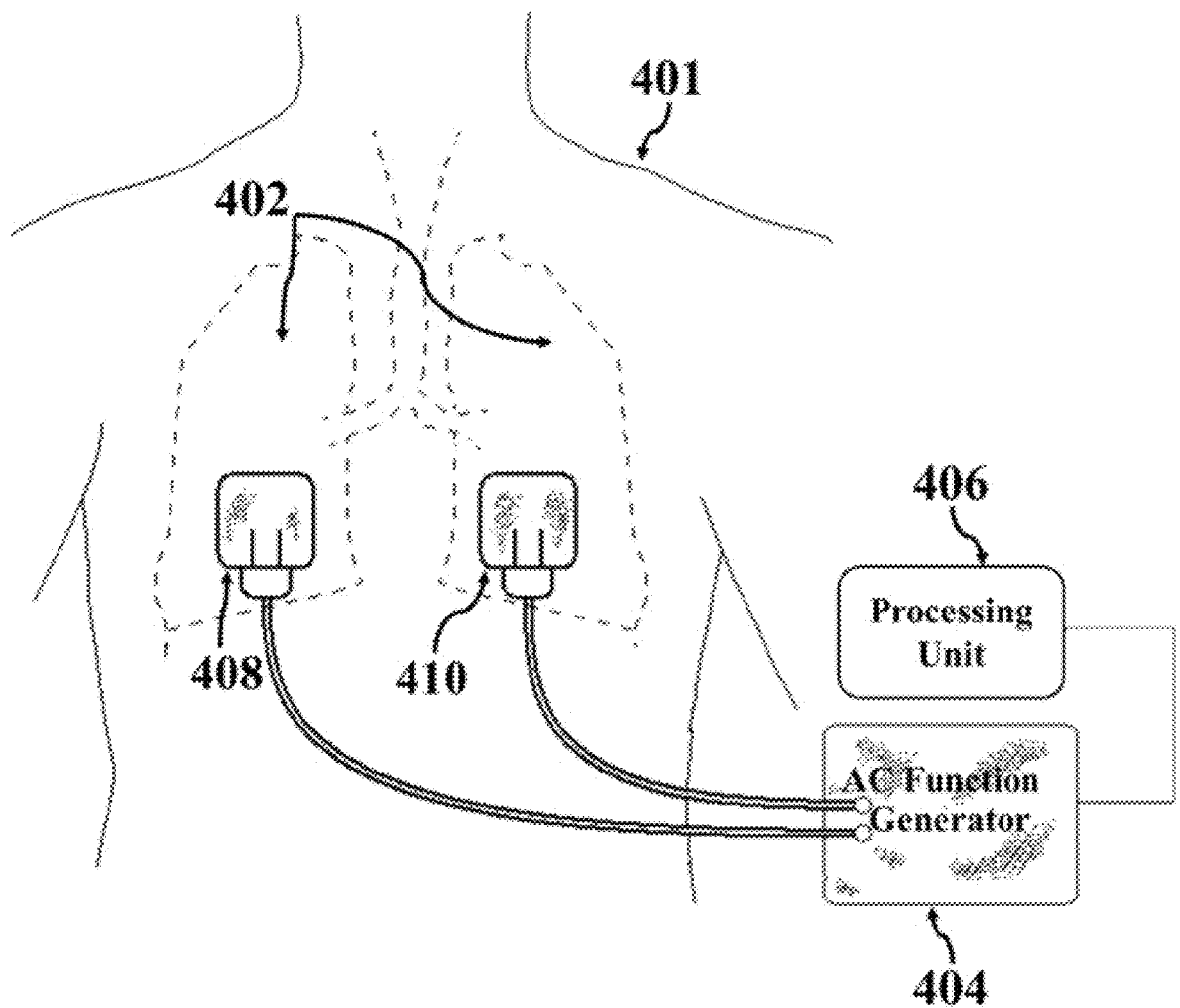
FIG. 4A shows an exemplary implementation of conducting an exemplary method for in-vivo suppressing clonal expansion of hyperactivated lymphocytes in an exemplary COVID-19 infected patient, consistent with one or more exemplary embodiments of the present disclosure.

In an exemplary implementation, placing a set of electrodes on skin of a patient infected by an inflammatory disease may include placing at least two electrodes on skin of a patient infected by an inflammatory disease. FIG. 4A shows an exemplary implementation of conducting method 100 for in-vivo suppressing clonal expansion of hyperactivated lymphocytes in exemplary COVID-19 infected patient 401, consistent with one or more exemplary embodiments of the present disclosure. Referring to this figure, putting a medium including a plurality of hyperactivated proliferative lymphocytes in contact with a set of electrodes (step 102) may include placing at least two electrodes 408 and 410 on skin of exemplary COVID-19 infected patient 401 adjacent to lung tissue 402. In an exemplary implementation, placing at least two electrodes 408 and 410 on skin of exemplary COVID-19 infected patient 401 may include putting at least one electrode 408 on skin of COVID-19 infected patient 401 at a location of a first portion of lung tissue 402 of COVID-19 infected patient 401 and putting at least one electrode 410 on skin of COVID-19 infected patient 401 at a location of a second portion of lung tissue 402 of COVID-19 infected patient 401.

In another exemplary implementation, placing a set of electrodes on skin of a patient infected by an inflammatory disease may include placing at least four exemplary electrodes on skin of a patient infected by an inflammatory disease allowing for applying AEF within an infected organ or tissue of the patient in various directions. In an exemplary implementation, placing a set of electrodes on skin of a patient infected by an inflammatory disease may include putting at least four electrodes over skin of the patient at four locations adjacent to an infected organ or tissue of the patient, where the infected organ or tissue of the patient may include a plurality of hyperactivated lymphocytes therein. As used herein, "locations adjacent to an infected organ or tissue" may refer to a location in a patient's body located within a distance of less than about 20 cm from the infected organ or tissue. In an exemplary embodiment, "locations adjacent to an infected organ or tissue" may refer to a location in a patient's body located within a distance of maximally 10 cm apart from a central part of the infected organ or tissue.

In an exemplary implementation, putting at least four electrodes over skin of the patient at four locations adjacent to an infected organ or tissue of the patient may include putting at least four electrodes over skin of a COVID-19 infected patient with a COVID-19 infected lung at respective four locations over skin of the COVID-19 infected patient adjacent to the COVID-19 infected lung. In an exemplary implementation, putting at least four electrodes over skin of a COVID-19 infected patient with the COVID-19 infected lung may include putting a first electrode and a second electrode of the at least four electrodes on skin of the COVID-19 infected patient at two respective locations on skin of the COVID-19 infected patient located around chest of the COVID-19 infected patient. In an exemplary implementation, putting the first electrode and the second electrode on skin of the COVID-19 infected patient may include putting the first electrode and the second electrode on a part of skin of the COVID-19 infected patient located either in front of the chest and/or behind the chest on back of the COVID-19 infected patient. In an exemplary implementation, putting the at least four electrodes over skin of the COVID-19 infected patient with the COVID-19 infected lung may further include putting a third electrode and a fourth electrode of the at least four electrodes on skin of the COVID-19 infected patient at two respective locations on skin of the COVID-19 infected patient located within a distance of less than 20 cm from the infected lung. In an exemplary implementation, the third electrode and the fourth electrode of the at least four electrodes may be placed on skin of the COVID-19 infected patient at two respective locations on skin of the COVID-19 infected patient located within a distance of less than 10 cm from the infected lung. In an exemplary implementation, the third electrode and the fourth electrode of the at least four electrodes may be placed at two respective locations of skin of the COVID-19 infected patient placed over at least one of chest, armpit, waist, shoulder, back and combinations thereof of the COVID-19 infected patient.

Figure 4B:
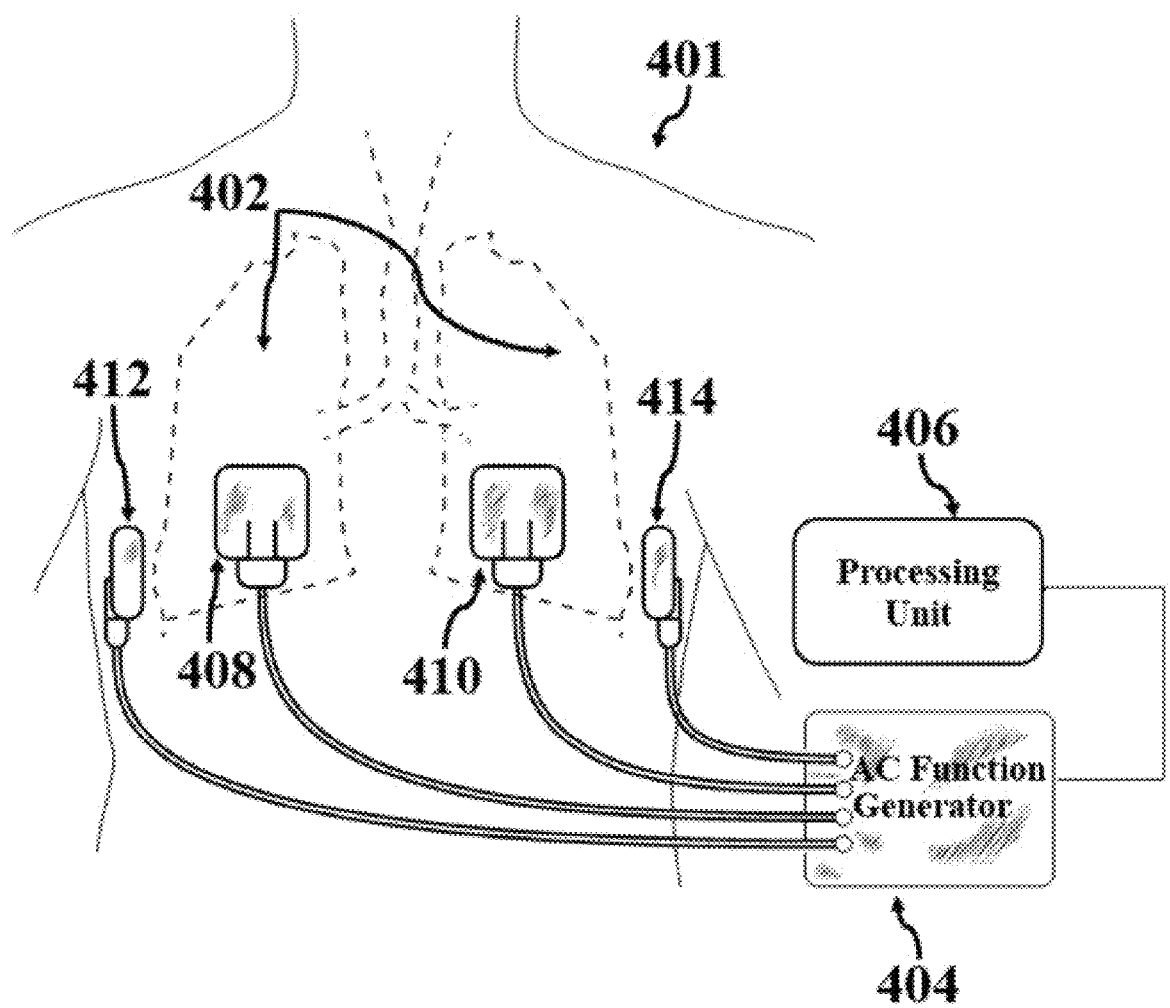
FIG. 4B shows another exemplary implementation of conducting an exemplary method for in-vivo suppressing clonal expansion of hyperactivated lymphocytes in an exemplary COVID-19 infected patient, consistent with one or more exemplary embodiments of the present disclosure.

FIG. 4B shows another exemplary implementation of conducting method 100 for in-vivo suppressing clonal expansion of hyperactivated lymphocytes in exemplary COVID-19 infected patient 401, consistent with one or more exemplary embodiments of the present disclosure. In an exemplary implementation referring to FIG. 4B, placing at least four electrodes on skin of a patient infected by an inflammatory disease may include putting at least two electrodes 408 and 410 on skin of COVID-19 infected patient 401 at two respective locations over chest of COVID-19 infected patient 401 on the front part of ribcage and putting at least two electrodes 412 and 414 on skin of COVID-19 infected patient 401 at respective two locations adjacent to lung tissue 402 of COVID-19 infected patient 401. In an exemplary implementation, putting at least two electrodes 412 and 414 on skin of COVID-19 infected patient 401 at respective two locations adjacent to lung tissue 402 of COVID-19 infected patient 401 may include putting at least two electrodes 412 and 414 at respective two locations of skin place over at least one of chest, armpit, waist, shoulder, back and combinations thereof of 412 and 414. In an exemplary implementation, at least two electrodes 412 and 414 may be place at two respective locations at two respective armpits of COVID-19 infected patient 401.

Referring to FIG. 1B, electrically stimulating a plurality of hyperactivated proliferative lymphocytes within an exemplary medium (step 104) may include connecting the set of electrodes in contact with the medium containing the plurality of hyperactivated proliferative lymphocytes to an AC function generator device (step 112) and generating an alternating electric field (AEF) within the medium by applying an AC voltage to the set of electrodes utilizing the AC function generator device (step 114). In an exemplary implementation, electrically stimulating the hyperactivated proliferative lymphocytes may include electrically stimulating the hyperactivated proliferative lymphocytes within an infected organ or tissue in a patient, for example, lung tissue 402 (FIGS. 4A and 4B) of COVID-19 infected patient 401. In an exemplary implementation, electrically stimulating the hyperactivated proliferative lymphocytes may include suppressing mitosis of the hyperactivated proliferative lymphocytes cells within the infected organ or tissue, for example, suppressing mitosis of hyperactivated proliferative lymphocytes cells in lung tissue 402 (FIGS. 4A and 4B) of COVID-19 infected patient 401.

In an exemplary implementation, electrically stimulating the hyperactivated proliferative lymphocytes may include connecting the at least two electrodes 408 and 410 to exemplary AC function generator device 404 (FIG. 4A). In an exemplary implementation, electrically stimulating the hyperactivated proliferative lymphocytes may include connecting the at least four electrodes 408, 410, 412, and 414 to exemplary AC function generator device 404 (FIG. 4B). In an exemplary embodiment, AC function generator device 404 may be similar to an exemplary AC function generator device utilized for in-vitro suppressing clonal expansion of hyperactivated lymphocytes described hereinabove.

In an exemplary implementation, generating an AEF within the medium by applying an AC voltage to the set of electrodes being in contact with the medium utilizing the AC function generator device (step 114) may include generating an AEF within the infected organ or tissue by applying an AC voltage to the at least two or four electrodes utilizing the AC function generator device. In an exemplary implementation, generating an AEF within the infected organ or tissue may include generating an AEF within lung tissue 402 of COVID-19 infected patient 401 by applying an AC voltage to at least two electrodes 408 and 410 or at least four electrodes 408, 410, 412, and 414 utilizing AC function generator device 404.

In an exemplary implementation, applying the AC voltage to at least two exemplary electrodes 408 and 410 or at least four exemplary electrodes 408, 410, 412, and 414 may include applying an AC voltage in a range between about 0.5 V/cm and about 7 V/cm with a constant frequency in a range between about 50 kHz and about 200 kHz to at least two exemplary electrodes 408 and 410 or at least four exemplary electrodes 408, 410, 412, and 414.

In an exemplary implementation, suppressing mitosis of hyperactivated proliferative lymphocytes cells within an exemplary medium, such as lung tissue 402 of COVID-19 infected patient 401 by electrically stimulating the hyperactivated proliferative lymphocytes (step 104) may be done for a pre-determined period of time. In an exemplary embodiment, the pre-determined period of time may include at least 20 hours in form of at least one of a continuous time interval, a plurality of intermittent time intervals, and combinations thereof. In an exemplary embodiment, the pre-determined period of time may include a plurality of time steps.

Referring again to FIG. 1B, electrically stimulating a plurality of hyperactivated proliferative lymphocytes within an exemplary medium (step 104) may further include stimulating the hyperactivated proliferative lymphocytes with respective mitotic spindles aligned in a plurality of directions by periodically changing a direction of the generated AEF in a plurality of directions within the medium (step 116). In an exemplary implementation, stimulating the hyperactivated proliferative lymphocytes with respective mitotic spindles aligned in a plurality of directions may include stimulating the hyperactivated proliferative lymphocytes with mitotic spindle aligned in a plurality of directions by periodically changing a direction of the generated AEF in the plurality of directions within the infected organ or tissue.

In an exemplary implementation, periodically changing the direction of the generated AEF in the plurality of directions within the infected organ or tissue, such as lung tissue 402 may include periodically switching of signal poles and ground poles of the applied AC voltage between at least two respective electrodes of at least four exemplary electrodes 408, 410, 412, and 414 at each time step of the intermittent time intervals of the pre-determined period of time. In an exemplary implementation, each time step of the pre-determined period of time may include a time interval between about 0.5 second and about 5 seconds of the pre-determined period of time. In an exemplary implementation, periodically changing the direction of the generated AEF in the plurality of directions within the infected organ or tissue, such as lung tissue 402 may include replacing one electrode of at least four exemplary electrodes 408, 410, 412, and 414 by another electrode of at least four exemplary electrodes 408, 410, 412, and 414 per each time step. In an exemplary implementation, periodically changing the direction of the generated AEF in the plurality of directions within the infected organ or tissue, such as lung tissue 402 may include replacing electrode 414 with one of electrodes 408, 410, and 412 per each time step. So, a direction of the generated AEF may be changed per each time step.

In an exemplary implementation, steps 114 and 116 of exemplary step 104 may be carried out by processing unit 406 utilizing AC function generator device 404. In an exemplary implementation, processing unit 406 may include a memory having processor-readable instructions stored therein and a processor. The processor may be configured to access the memory and execute the processor-readable instructions.

In an exemplary implementation, the processor may be configured to perform a method by executing the processor-readable instructions. In an exemplary implementation, the method may include conducting steps 114 and 116 of exemplary step 104. In an exemplary implementation, the method may include generating an AEF within an exemplary medium by applying an AC voltage to an exemplary set of electrodes being in contact with the medium utilizing AC function generator device 404 (step 114) and periodically changing a direction of the generated AEF in a plurality of directions within the medium utilizing AC function generator device 404 (step 116).

Figure 5:
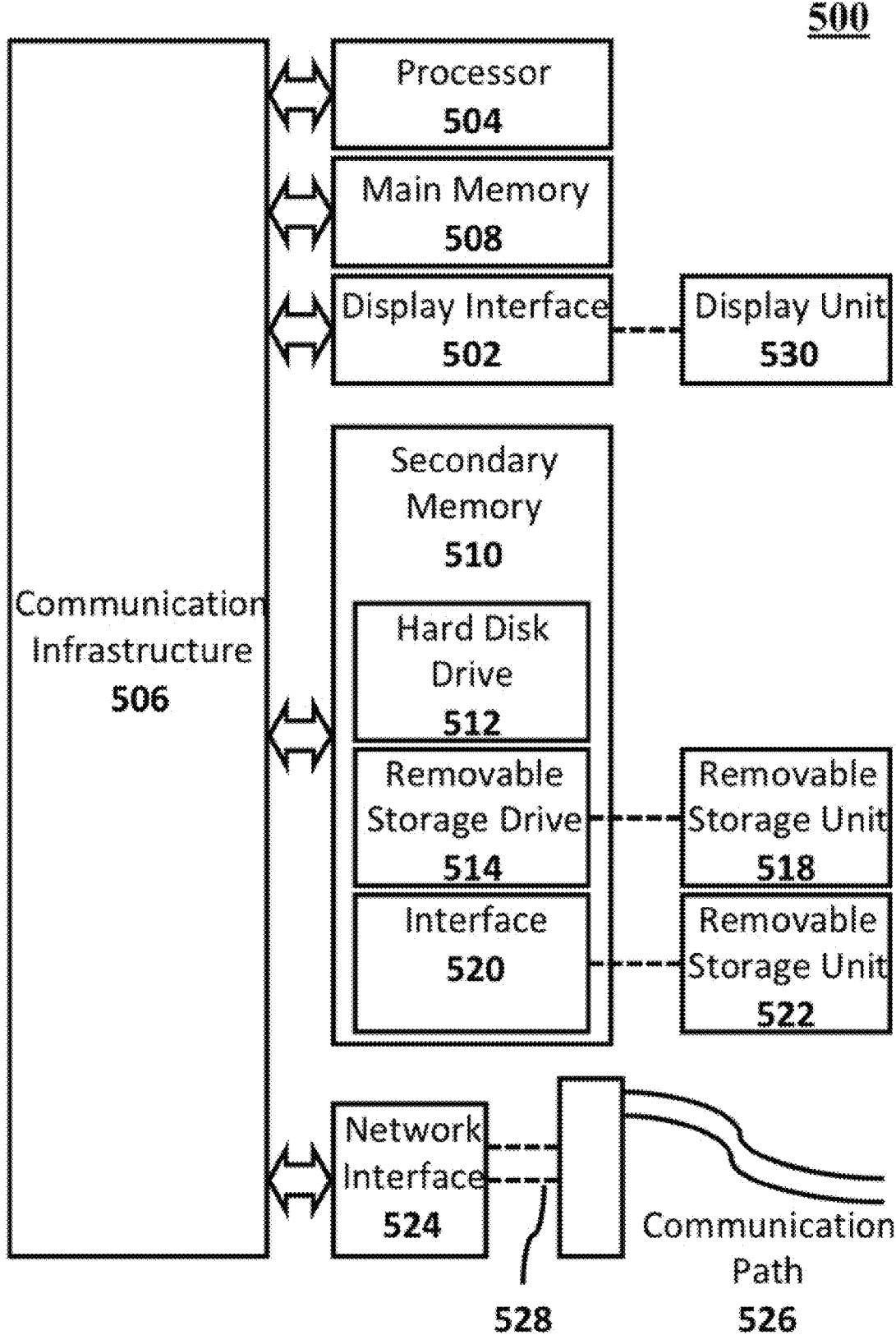
FIG. 5 shows an example computer system in which an embodiment of the present disclosure, or portions thereof, may be implemented as computer-readable code, consistent with one or more exemplary embodiments of the present disclosure.

FIG. 5 shows an example computer system 500 in which an embodiment of the present disclosure, or portions thereof, may be implemented as computer-readable code, consistent with one or more exemplary embodiments of the present disclosure. For example, computer system 500 may include an example of processing unit 406 illustrated in FIGS. 4A and 4B, and steps 114 and 116 of exemplary step 104 presented in FIG. 1B, may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIGS. 1B, 4A and 4B.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the present disclosure is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in method 100 illustrated by FIGS. 1A and 1B, discussed above. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

EXAMPLE 1: FABRICATING AEF STIMULATION BIOCHIP

In this example, an AEF stimulation biochip similar to exemplary biochip 200 was prepared. A glass substrate was cleaned using piranha solution ($H_2SO_4:H_2O_2$ with a volume ratio of 2:1, respectively). Then, a layer of Cr with a thickness of about 20 nm was deposited on the substrate using RF sputtering procedure and a layer of Au with a thickness of about 100 nm was deposited on the Cr layer using RF sputtering procedure. The Cr layer was used in order to enhance the Au layer adhesion to the glass substrate. Using standard photolithography, 8 electrodes were patterned on surface of Au coated glass. The patterned electrodes were passivated (electrically insulated) using a 4 μm layer of polydimethylsiloxane (PDMS) by spin coating at 6000 rpm for 5 minutes. The biochip contains eight electrodes designed in a circular pattern with an inner radius of 2 cm to attain symmetrical electric field distribution in four directions of electric field stimulation.

EXAMPLE 2: AEF STIMULATION OF ARTIFICIALLY ACTIVATED PBMCS

In this example, peripheral blood mononuclear cells (PBMCs) were isolated from healthy donors, followed by artificially being activated using lymphocyte expansion kits for mimicking lymphocytes clonal expansion by activating PBMCs. It should be noted that lymphocytes are one of subsets of white blood cells with mitosis capability. When lymphocytes are activated by external physicochemical signals, they form a cluster of cells and then are expanded. In case of T and B lymphocytes, such a phenomenon is called clonal expansion in which first activated cell produces many copies of itself with the same antigen properties. In order to mimic expansion of WBCs, T and B activation kits were utilized to artificially trigger expansion of lymphocytes in PBMCs of blood in-vitro.

Here, whole blood was obtained through a venipuncture technique from each person. PBMCs were isolated from the whole blood using density gradient centrifugation (DGC) method and then divided into four groups, including a first group of non-activated PBMCs without any external stimulation (intact WBCs are imaged as the control group), a second group of activated PBMCs, in which WBCs may began to expand using commercial activating kits for T and B cells, a third group of activated PBMCs stimulated by AEF (activated PBMCs+AEF), and a fourth group of activated PBMCs treated by Dexamethasone with a dosage of 4 mg/ml (PBMC+Dexamethasone). In this regard, an effect of AEF in suppressing clonal expansion would also be compared to dexamethasone (conventional immunosuppressor drug). For activation of lymphocytes, isolated PBMCs were cultured inside a cell culture medium and their lymphocytes were activated using an expansion kit. Activated cells were incubated for 5 days to ensure lymphocytes activation. For AEF stimulation of activated cells, activated cells were dropped on surface of exemplary fabricated biochip in EXAMPLE 1 hereinabove and stimulated using AEF stimulation according to exemplary method 100 for 48 hours. AEF stimulation of cells caused apoptosis in clusters of activated lymphocytes during cell division. FOR AEF stimulation of activated cells, exemplary fabricated biochip was connected to an RF function generator at 100 kHz sinusoid of 3 V/cm electric field amplitude. Effect of applying AEF on suppressing expansion of lymphocytes was evaluated by time-lapse imaging, viability, and apoptosis assays as well as flow cytometry technique. Moreover, amount of three major cytokines (TNF-alpha, INF-gamma, IL-6) after AEF stimulation was also measured using ELISA method.

Figure 6A:
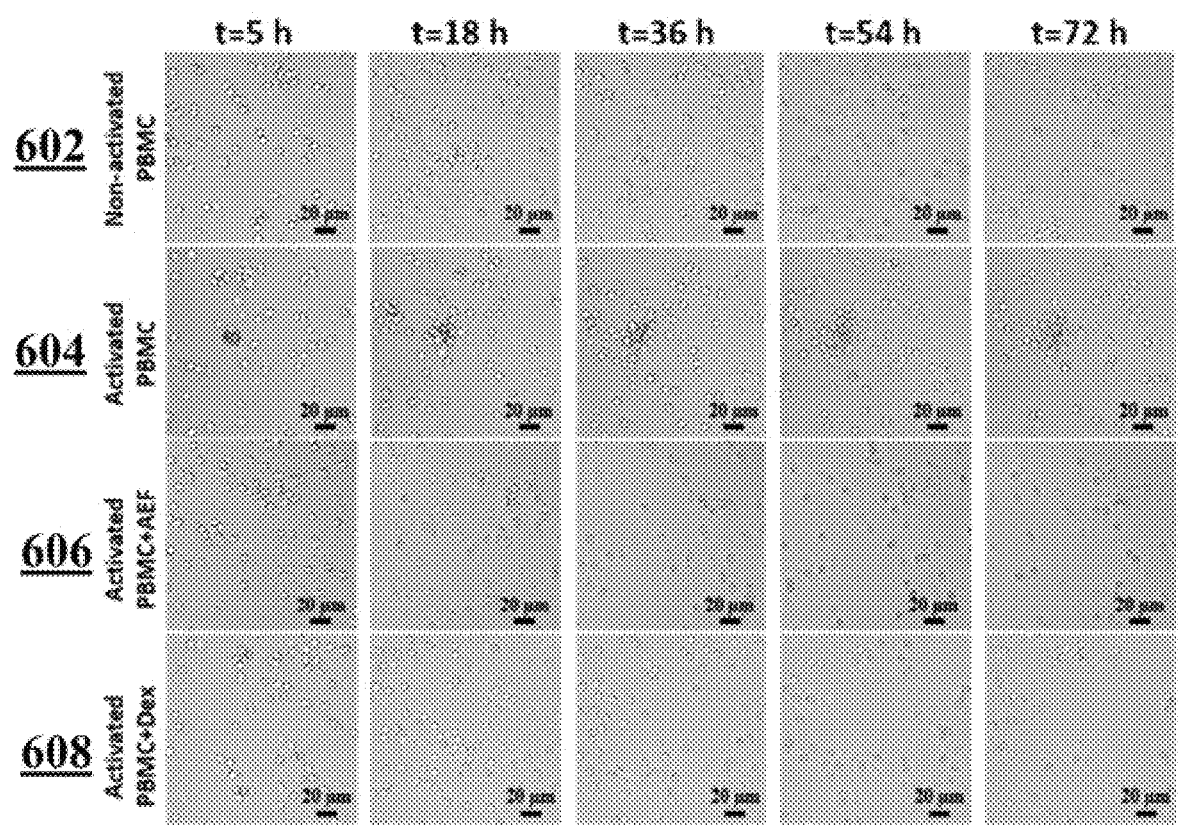
FIG. 6A shows time-lapse imaging for evaluation of lymphocyte cluster formation inside immune cell activation medium via for exemplary Non-activated PBMCs, Activated PBMCs, Activated PBMCs+AEF, and Activated PBMCs+Dexamethasone(DEX), consistent with one or more exemplary embodiments of the present disclosure.

Time-Lapse Imaging Analysis:

To analyze effect of AEF stimulation to suppress proliferation of exemplary activated lymphocytes, time-lapse imaging from PBMCs at different times was used. FIG. 6A shows time-lapse imaging for evaluation of lymphocyte cluster formation inside immune cell activation medium via for Non-activated PBMCs 602, Activated PBMCs 604, Activated PBMCs+AEF 606, and Activated PBMCs+Dexamethasone (DEX) 608, consistent with one or more exemplary embodiments of the present disclosure. As may be seen, in case of intact WBCs (Non-activated PBMCs), no cluster formation could be seen after 72 hours as all cells are moving alone. But, in group of activated PBMCs, small immune cell aggregations could be tracked, which rapidly grow in colony size and cover whole surface after 20 hours that confirm clonal expansion of activated lymphocytes. When cells are simultaneously treated AEF, no growth of cell clusters could be seen, which shows that even activated cells were not able to be expanded. Such antiproliferative immunosuppressing result could also be tracked in activated PBMCs+Dexamethasone group. This outcome corroborates that both AEF and Dexamethasone have a similar function in suppressing mitosis process of activated lymphocytes.

Figure 6B:
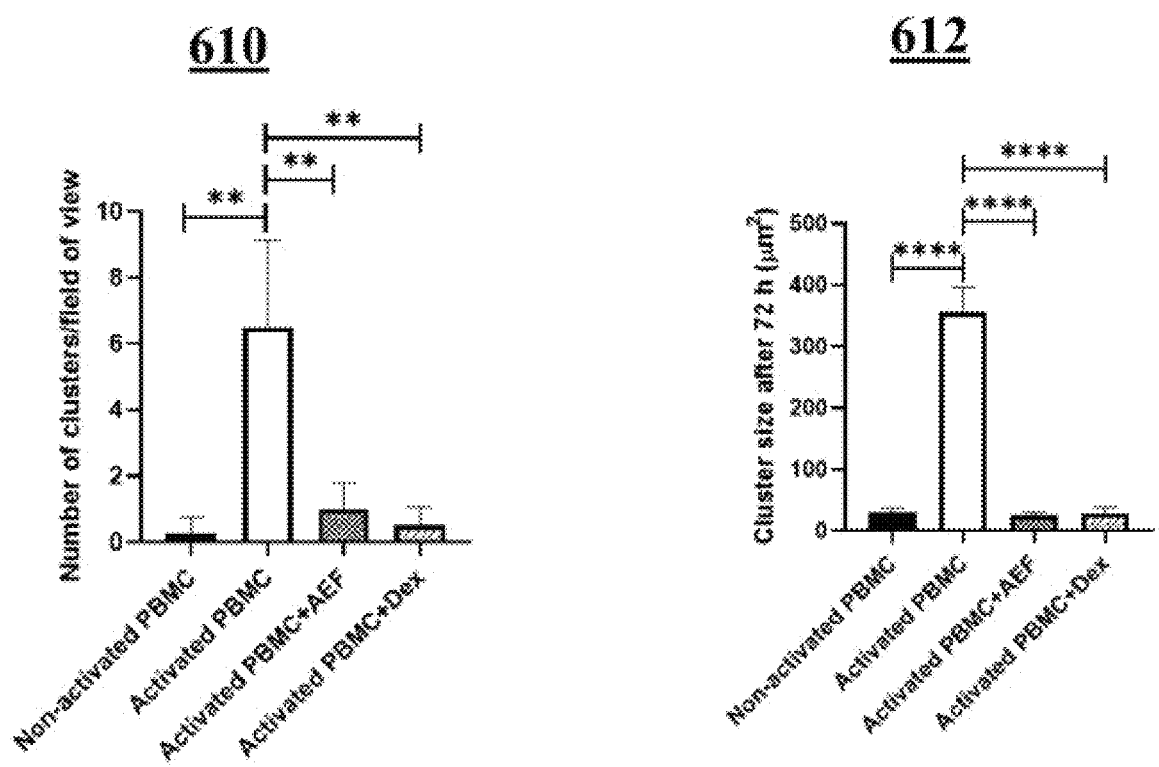
FIG. 6B shows number of clusters/field of view and cluster size after 72 hours analyzed by time-lapse imaging for exemplary Non-activated PBMCs, Activated PBMCs, Activated PBMCs+AEF, and Activated PBMCs+Dexamethasone(DEX), consistent with one or more exemplary embodiments of the present disclosure.

FIG. 6B shows number of clusters/field of view (diagram 610) and cluster size after 72 hours (diagram 612) analyzed by time-lapse imaging for Non-activated PBMCs, Activated PBMCs, Activated PBMCs+AEF, and Activated PBMCs+Dexamethasone (DEX) (where, "*" indicates p<0.05, "" indicates p<0.01, "*" indicates p<0.001, and "****" indicates p<0.0001), consistent with one or more exemplary embodiments of the present disclosure. It may be seen that the highest number of clusters were observed in activated PBMCs. These clusters were moderately larger in comparison with clusters formed in 3 other groups.

Figure 6C:
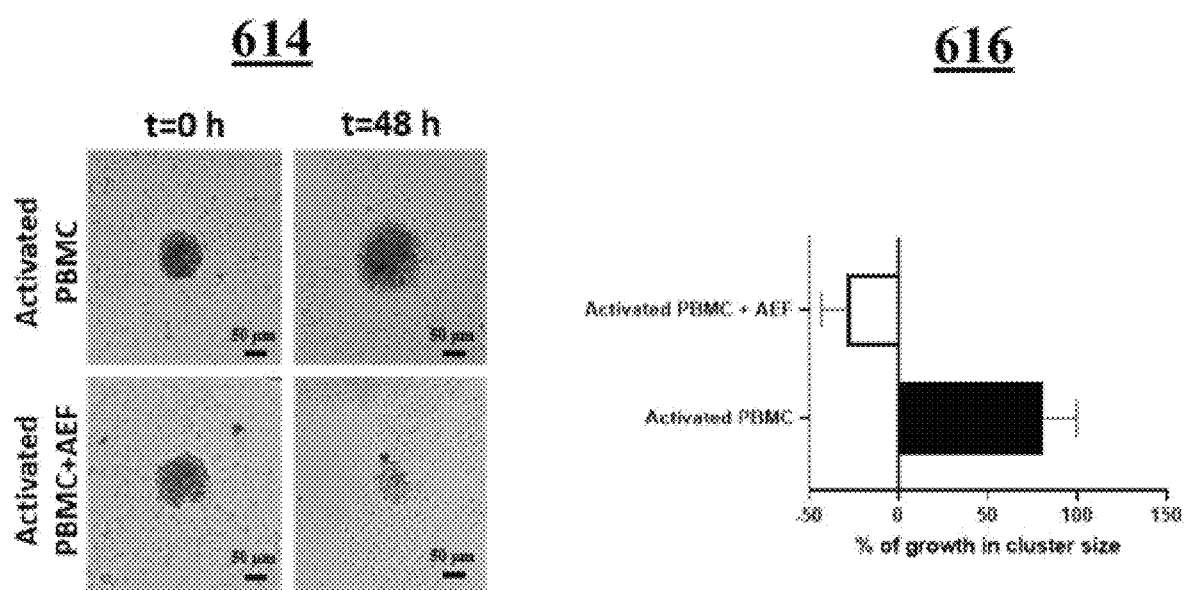
FIG. 6C shows time-lapse imaging and percentage of growth in cluster size for stimulated activated lymphocyte clusters by AEF in comparison with activated PBMCs after 48 hours, consistent with one or more exemplary embodiments of the present disclosure.

For more elaboration, AEF stimulation was applied on activated immune cells after 5 days. During these five days, clonal expansion clusters of immune cells were formed. Then, cluster size and their abundance were imaged and analyzed after 48 hours of AEF treatment via time-lapse microscopy. FIG. 6C shows time-lapse imaging (part 614) and percentage of growth in cluster size (diagram 616) for stimulated activated lymphocyte clusters by AEF in comparison with activated PBMCs after 48 hours, consistent with one or more exemplary embodiments of the present disclosure. Contrary to continuous growth of cell clusters in cohort of activated PBMCs, proliferation and expansion of activated PBMCs were strongly suppressed by AEF stimulation. As presented in FIG. 6C, average cluster size shows an increase of about 81% after 48 hours for non-AEF treated group, while growth of clusters in electrically stimulated group has been dropped by about 31%. These results confirm that suppressive effect of AEF stimulation is applicable for expanding activated lymphocytes.

Figure 7:
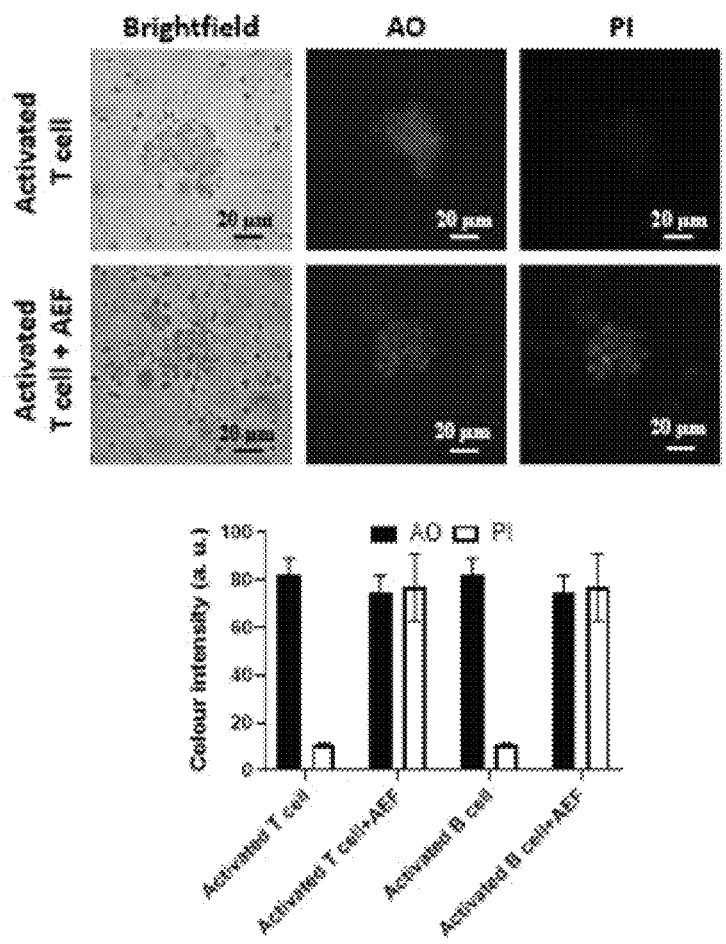
FIG. 7 shows immunofluorescence imaging of PI uptake in exemplary activated lymphocytes by 48 hours of AEF stimulation in comparison with non-stimulated control group, consistent with one or more exemplary embodiments of the present disclosure.

Viability of Stimulated Clusters and Non-Activated WBCs:

AO/PI staining as well as apoptosis assay by Annexin V/PI flow cytometry technique was carried out to analyze correlation between cellular viability and size reduction of treated clusters. Viability and apoptosis assays were performed separately on lymphocytes, including B and T cells. FIG. 7 shows immunofluorescence imaging of PI uptake in activated lymphocytes by 48 hours of AEF stimulation in comparison with non-stimulated control group, consistent with one or more exemplary embodiments of the present disclosure. Based on image analysis, all of two WBC subsets after AEF stimulation show a noticeable increase in expression of the PI dye, which is an indicator of membrane rupture and cell death. No PI uptake could be tracked in the control groups representing viability of cells.

Figure 8:
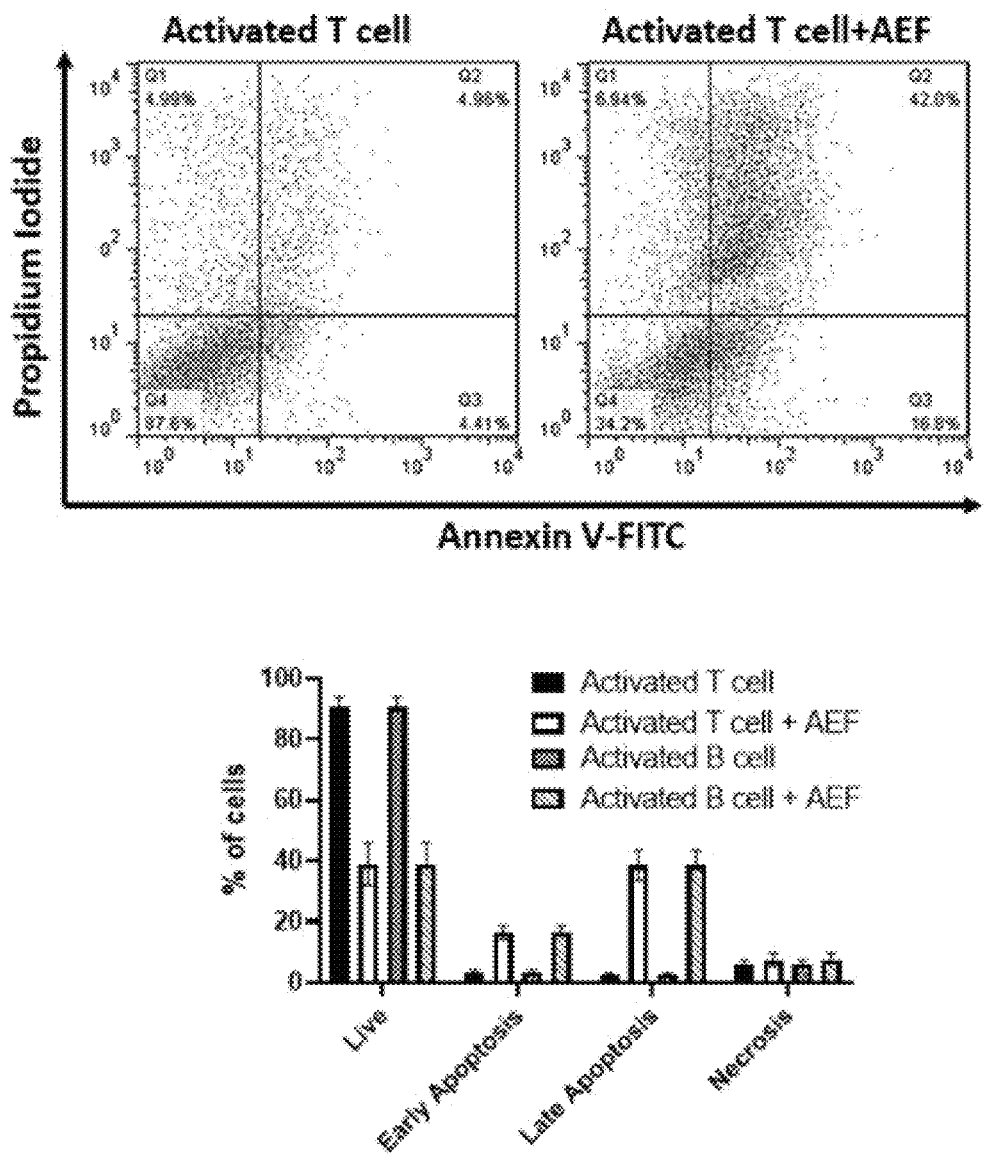
FIG. 8 shows Annexin V/PI assay results for exemplary activated lymphocytes stimulated by AEF in comparison with non-stimulated control group, consistent with one or more exemplary embodiments of the present disclosure.

FIG. 8 shows Annexin V/PI assay results for activated lymphocytes stimulated by AEF in comparison with non-stimulated control group, consistent with one or more exemplary embodiments of the present disclosure. An increase in percentage of activated lymphocytes in apoptosis phase that may be caused by AEF may be seen. A negligible difference was observed in cells undergoing necrosis in both groups. In harmony with results of AO/PI, flow cytometry results also show a significant reduction in fraction of live cells for AEF treated group in which most of cells entered into early and late apoptosis phase. As presented in FIG. 8, necrosis portion of cells is roughly the same before and after electric field treatment. This phenomenon corroborates non-necrosis induction of AEF on expanding immune cells because based on AEF mechanism, cells undergo apoptosis, and sudden death or necrosis does not happen.

Figure 9:
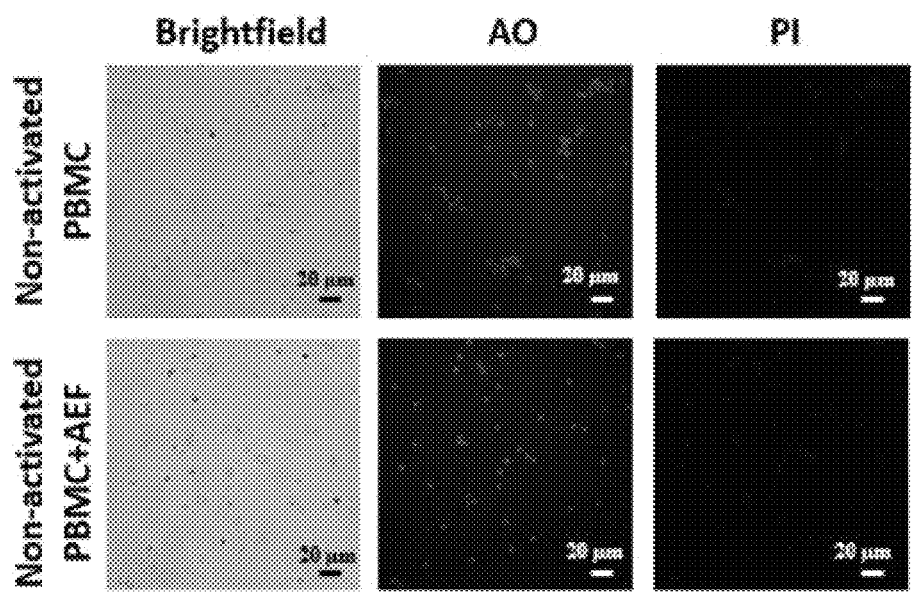
FIG. 9 shows immunofluorescence imaging assayed by AO/PI staining in exemplary groups of control non-activated PBMCs and AEF-stimulated non-activated PBMCs, consistent with one or more exemplary embodiments of the present disclosure.
Figure 10:
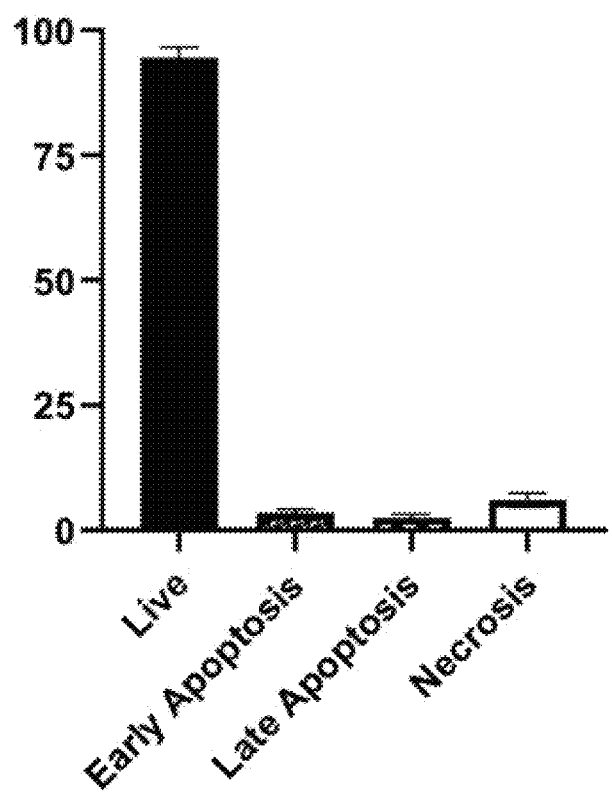
FIG. 10 shows results of Annexin V/PI test for exemplary non-activated immune cells after 48 hours of AEF treatment, consistent with one or more exemplary embodiments of the present disclosure.

Additionally, effect of AEF on non-activated white blood cells was evaluated by live/dead staining and apoptosis assay. FIG. 9 shows immunofluorescence imaging assayed by AO/PI staining in groups of control non-activated PBMCs and AEF-stimulated non-activated PBMCs, consistent with one or more exemplary embodiments of the present disclosure. Immunofluorescence imaging demonstrates negligible PI uptake in both groups of control and AEF-stimulated non-activated PBMCs due to effectiveness of AEF on dividing cells. There is no sign of cell clustering on CTRL group since cells are intact and no activating kit was used. As presented in FIG. 9, no PI uptake could be traced in CTRL WBCs before or after electrical stimulation. This evidence corroborates the fact that AEF only impacts proliferative cells. FIG. 10 shows results of Annexin V/PI test for non-activated immune cells after 48 hours of AEF treatment, consistent with one or more exemplary embodiments of the present disclosure. In harmony with AO/PI assay shown in FIG. 9, results of Annexin V/PI test also show no apoptosis in non-activated immune cells after 48 hours of AEF treatment.

Figure 11:
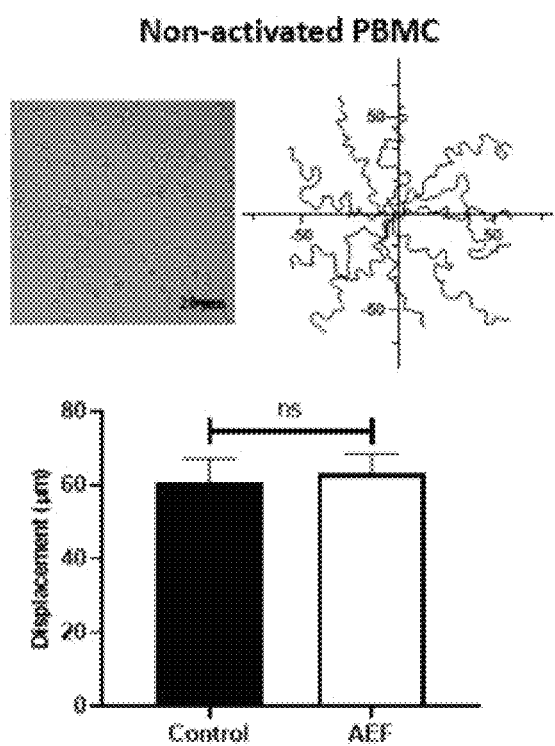
FIG. 11 shows cell plotted trajectories for exemplary non-activated PBMCs in control group and AEF-stimulated non-activated PBMCs group in addition to respective diagrams of displacement and velocity, consistent with one or more exemplary embodiments of the present disclosure.
Figure 11:
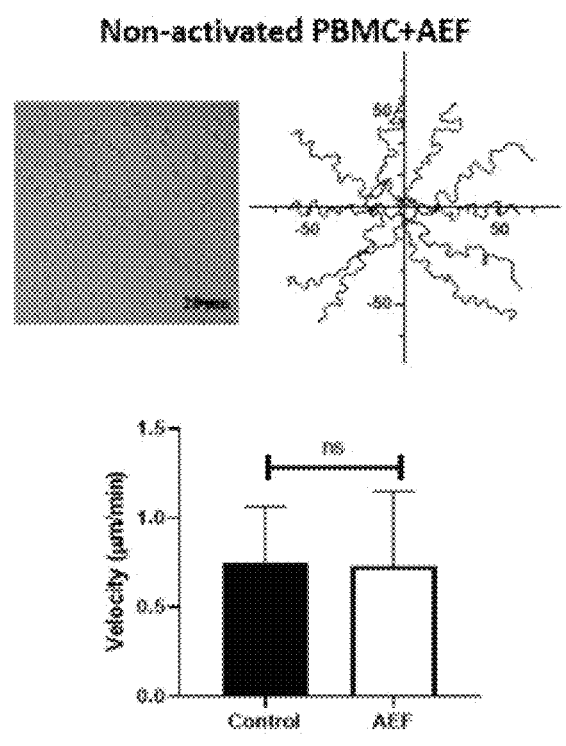

Trajectory of WBCs as well as their displacement and velocity were also analyzed for non-activated WBCs in the presence and absence of AEF. FIG. 11 shows cell plotted trajectories for non-activated PBMCs in control group (designated by 1102) and AEF-stimulated non-activated PBMCs group (designated by 1104) in addition to respective diagrams of displacement (diagram 1106) and velocity (diagram 1108), consistent with one or more exemplary embodiments of the present disclosure. No significant difference was observed between displacements and velocities and natural moving behavior in these two groups.

Figure 12:
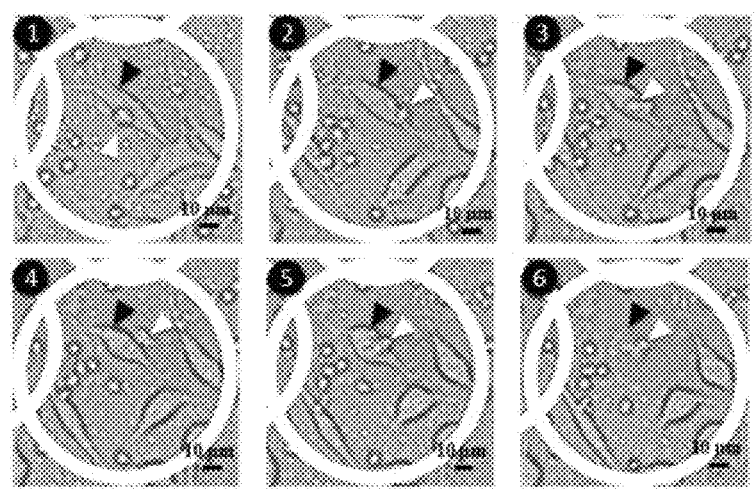
FIG. 12 shows time-lapse imaging on interaction of exemplary electrically stimulated WBCs from a human donor with MDA-MB-231 cancer cell line and number of attacks by WBCs to foreigner MDA-MB-231 cells for control and stimulated WBCs, consistent with one or more exemplary embodiments of the present disclosure.
Figure 12:
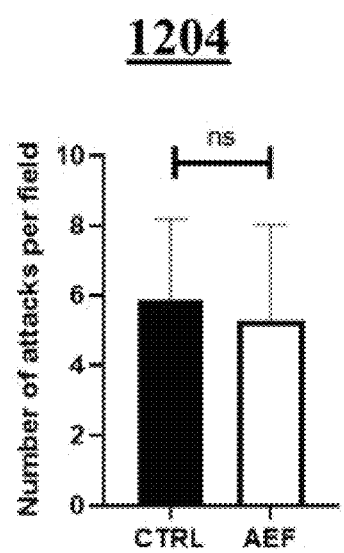

For further clarification, effect of electric field on invasive function of WBCs toward pathological threats was assessed. Time-lapse imaging was utilized to inspect interaction of WBCs with exemplary foreigner MDA-MB-231 cells. Due to HLA mismatch between MDA-MB-231 cells and donor WBCs, it is supposed that cytotoxic T cells (CTLs) as well as natural killer cells (NK cells) are activated and invade the MDA-MB-231 cells. FIG. 12 shows time-lapse imaging on interaction of electrically stimulated WBCs from a human donor with MDA-MB-231 cancer cell line (part 1202) and number of attacks by WBCs to foreigner MDA-MB-231 cells for control and stimulated WBCs (diagram 1204), consistent with one or more exemplary embodiments of the present disclosure. Based on the results, there is no significant alteration in number of attacks by immune cells to MDA-MB-231 cells which corroborates safety of the applied AEF on normal function of immune cells.

Effect of AEF on Lymphocyte Subsets Analyzed by Flow Cytometry:

Flow cytometry technique was employed to investigate detailed effects of AEF on each subset of lymphocytes. Both of B and T cell activation and expansion kits were simultaneously applied to a blood sample of a healthy donor. Cells were then (after 5 days) treated with AEF stimulation for 4 days, and number of CD8 and CD4 positive cells (T cell markers) and CD19 cells (B cell marker) were counted by a flow cytometer. Obtained results were compared with similar results for activated but non AEF treated cells as a control group.

Figure 13A:
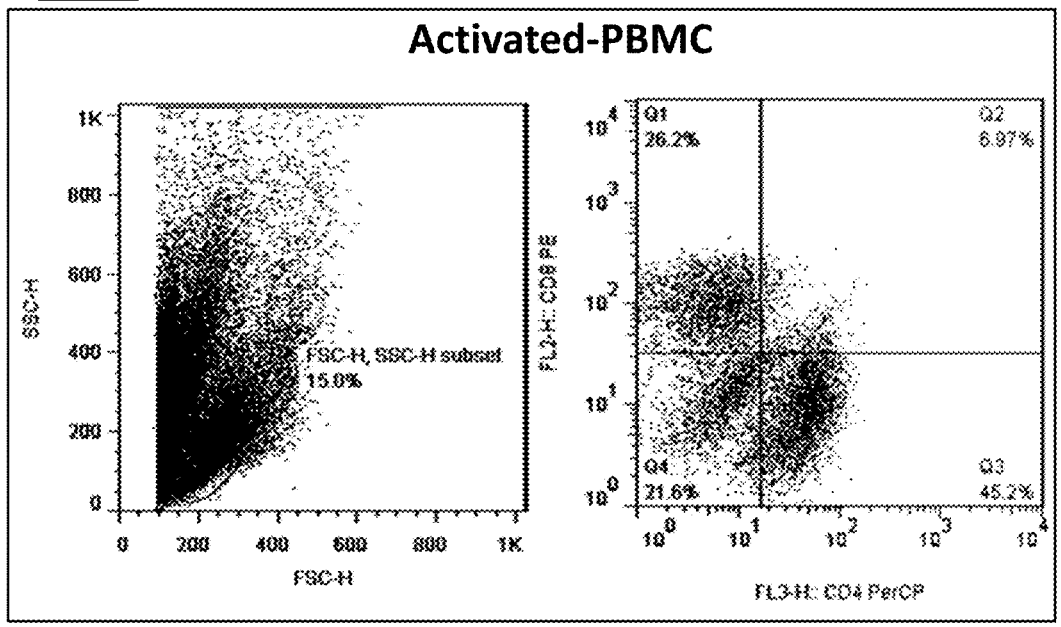
FIG. 13A shows flow cytometry analysis results for exemplary activated PBMCs exposed to AEF for 4 days compared to control group, consistent with one or more exemplary embodiments of the present disclosure.
Figure 13A:
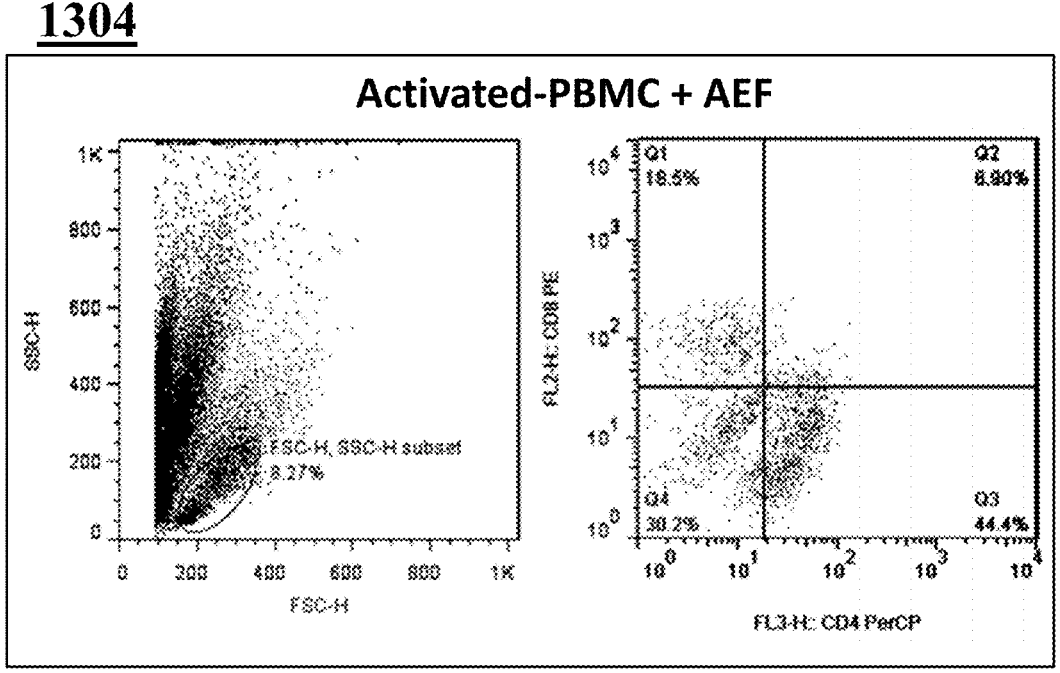
Figure 13B:
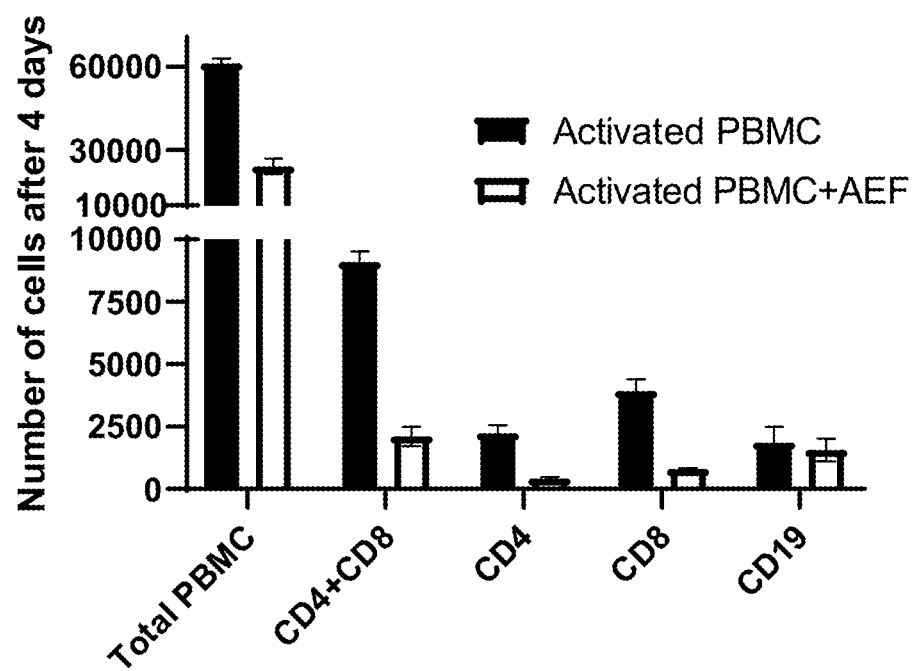
FIG. 13B shows number of cells for each group of lymphocytes in PBMC after 4 days for activated PBMCs (control group) and activated PBMCs stimulated by AEF, consistent with one or more exemplary embodiments of the present disclosure.
Figure 13C:
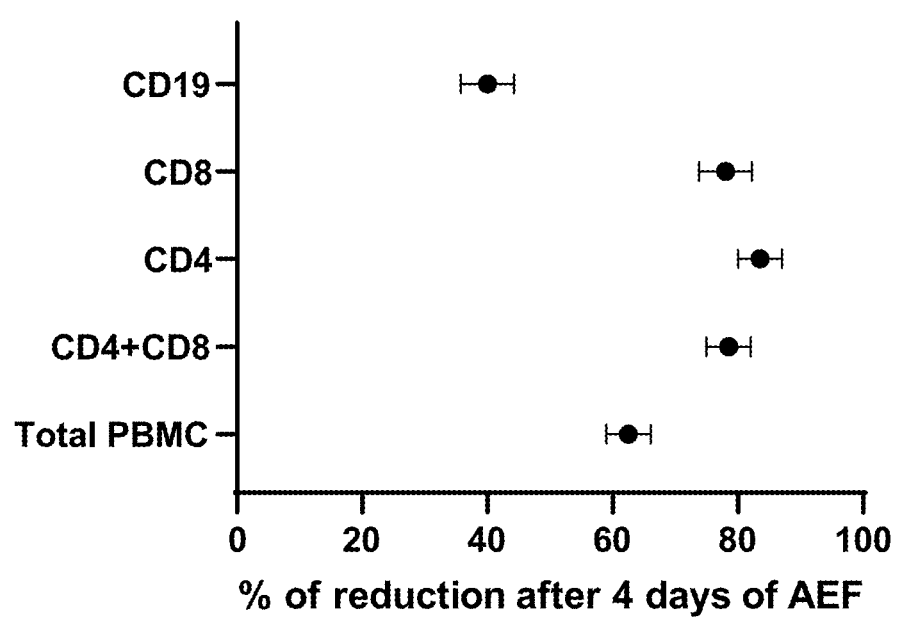
FIG. 13C shows percentage of reduction in number of cells for each group of lymphocytes in PBMC after 4 days for activated PBMCs (control group) and activated PBMCs stimulated by AEF, consistent with one or more exemplary embodiments of the present disclosure.

FIG. 13A shows flow cytometry analysis results for activated PBMCs exposed to AEF for 4 days (designated by 1304) compared to control group (designated by 1302), consistent with one or more exemplary embodiments of the present disclosure. Flow cytometry analysis confirmed reduction of activated PBMCs exposed to AEF for 4 days compared to their control group. FIG. 13B shows number of cells for each group of lymphocytes in PBMC after 4 days for activated PBMCs (control group) and activated PBMCs stimulated by AEF, consistent with one or more exemplary embodiments of the present disclosure. Furthermore, FIG. 13C shows percentage of reduction in number of cells for each group of lymphocytes in PBMC after 4 days for activated PBMCs (control group) and activated PBMCs stimulated by AEF, consistent with one or more exemplary embodiments of the present disclosure.

Based on FIG. 13A, population of all pre-activated lymphocyte subsets was drastically reduced after AEF treatment (FIG. 13B). For instance, T lymphocytes, including CD8+ and CD4+ cells, have lost about 80% of their population after AEF stimulation and this fraction for B cells is about 40% (FIG. 13C). It confirms that proliferation of expanding cells was suppressed by AEF stimulation. When activated cells lose their ability to expand and are arrested in mitosis phase of their cell cycle due to an abnormal division, they enter an apoptosis phase. Therefore, number of cells in the AEF treated group becomes lower than the control activated and expanding cells. Moreover, T cells, including CD4+ and CD8+ cells, are more affected by the electric field treatment. This is due to a fact that T cells expand faster than B cells, and as a result, AEF stimulation has more suppressing impact on their division.

Inspecting Cytokine Reduction after Electric Field Treatment:

Cytokine production by immune cells was analyzed in both groups of activated control and AEF-treated cells. Firstly, cells were activated for 5 days. In the activated PBMC+AEF group, cells were under AEF stimulation for about 4 days. During these 4 days, non-AEF treated group was just kept in an incubator. At the end of test, solution medium of both groups was collected and analyzed by enzyme linked immunosorbent assay (ELISA) method.

Figure 14:
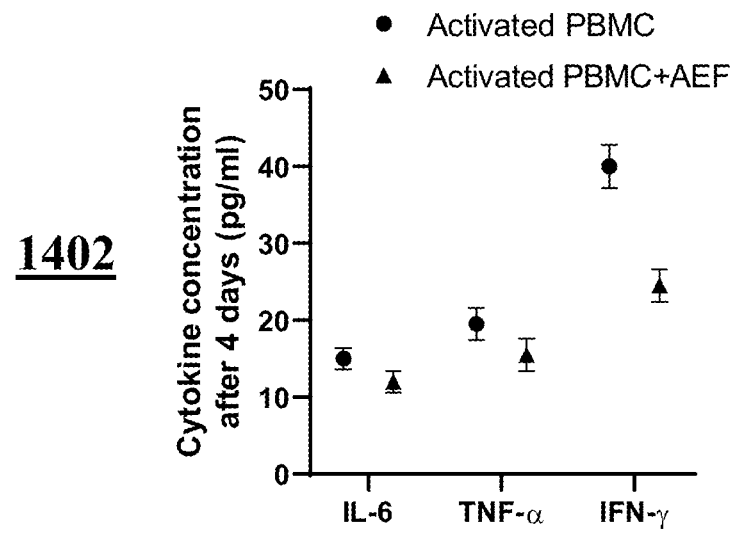
FIG. 14 shows concentration of inflammatory cytokines in exemplary activated PBMCs (control group) and activated PBMCs stimulated by AEF, daily percentage of reduction for each respective cytokine, and percentage of reduction in concentration of inflammatory cytokines, cluster size, and number of clusters after 4 days of AEF treatment, consistent with one or more exemplary embodiments of the present disclosure.
Figure 14:
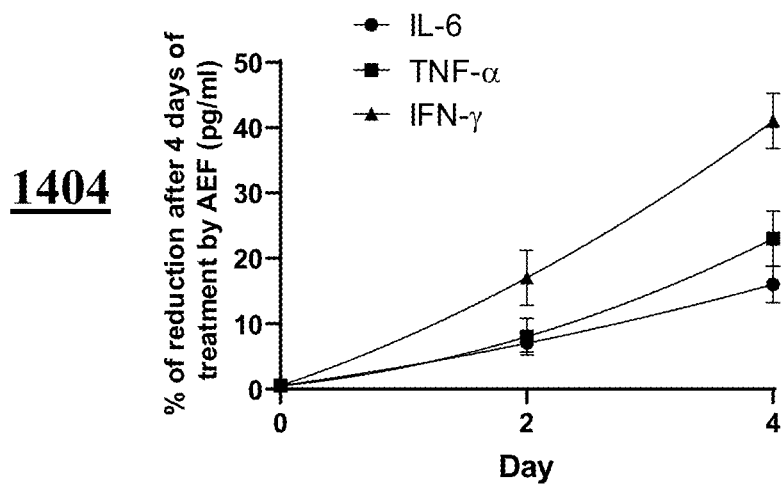
Figure 14:
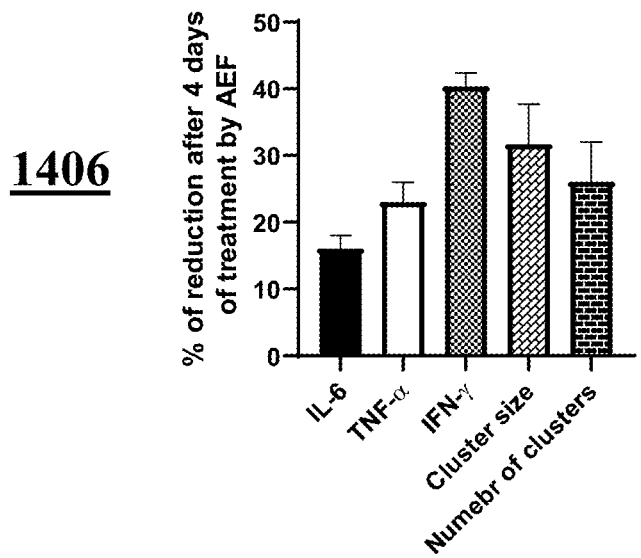

Although many cytokines are produced and play functional roles in post-activated immune cells, there are three main cytokines, including IL-6, TNF-$\alpha$, and IFN-$\gamma$ that are produced by lymphocytes and play the main role especially in COVID-19 disease. FIG. 14 shows concentration of inflammatory cytokines in activated PBMCs (control group) and activated PBMCs stimulated by AEF (diagram 1402), daily percentage of reduction for each respective cytokine (diagram 1404), and percentage of reduction in concentration of inflammatory cytokines, cluster size, and number of clusters (diagram 1406) after 4 days of AEF treatment, consistent with one or more exemplary embodiments of the present disclosure. Based on FIG. 14, all three major cytokines have shown a considerable reduction after 4 days of electric field stimulation. As presented in diagram 1406, the most cytokine reduction was attributed to IFN-$\gamma$ with about 40% and the least for IL-6 with about 16% (and about 25% for TNF-$\alpha$). This decrease is associated with reduced number of immune cells after suppression of their proliferation by AEF. Hence, number of clusters, as well as their size, was assessed for the two groups.

Figure 15:
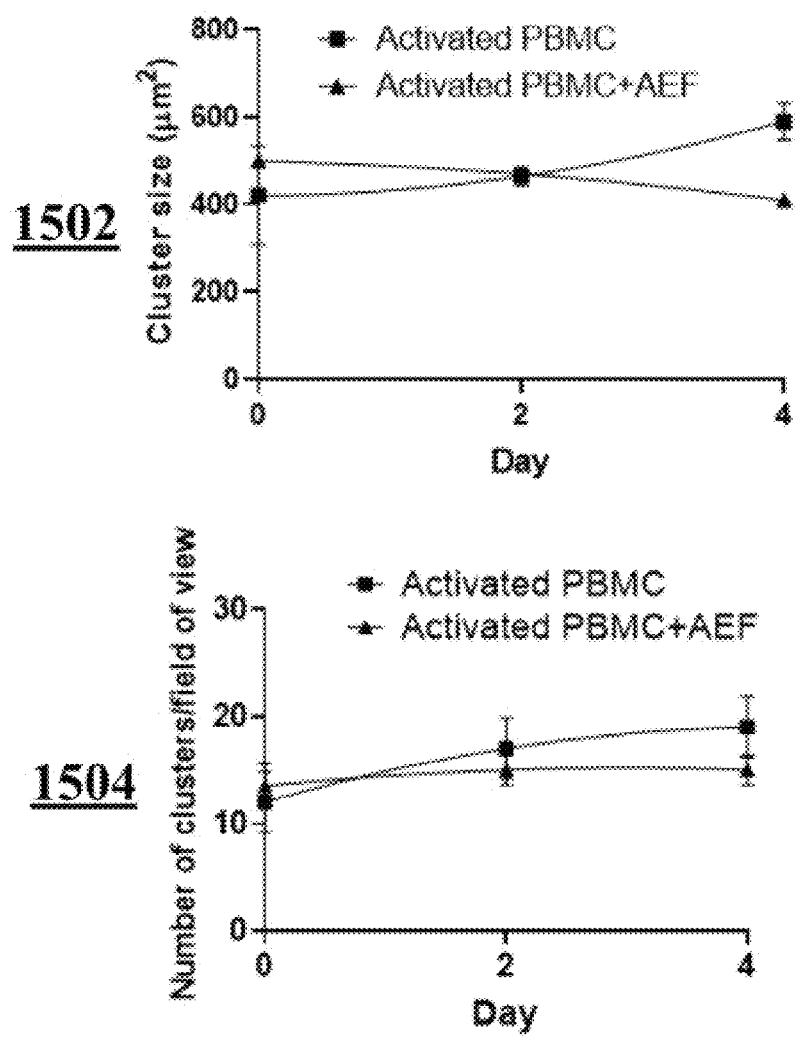
FIG. 15 shows comparison between daily amount of cluster size and number of clusters per field of view for exemplary activated PBMCs in control and AEF-stimulated groups, consistent with one or more exemplary embodiments of the present disclosure.

FIG. 15 shows comparison between daily amount of cluster size (diagram 1502) and number of clusters per field of view (diagram 1504) for activated PBMCs in control and AEF-stimulated groups, consistent with one or more exemplary embodiments of the present disclosure. As shown in FIG. 15 and in harmony with results of cytokine profiling, a reductive trend could be observed in the case of cluster size and abundance by 32% and 26% (diagram 1406 of FIG. 14), respectively.

EXAMPLE 3: EFFECT OF AEF ON SUPPRESSING CLONAL EXPANSION AND CYTOKINE PRODUCTION IN COVID-19 PATIENTS

In this example, in-vitro AEF stimulating of WBCs derived from COVID-19 patients with severe inflammation and cytokine storm was carried out according to exemplary method 100 utilizing an exemplary fabricated biochip according to EXAMPLE 1 hereinabove similar to exemplary biochip 200. Human blood samples were collected from five patients with COVID-19 disease to assess efficacy of applying alternating electric field on suppressing activation and expansion of immune cells and consequent reduction in cytokine production. Patients had not received any medication prior to blood sampling. After blood sampling and isolation of WBCs (PBMCs) using density gradient centrifugation method, cells were divided into two cohorts of a control group (without AEF treatment) and a group of electrically stimulated cells. Both groups were under analysis for 4 days.

Figure 16:
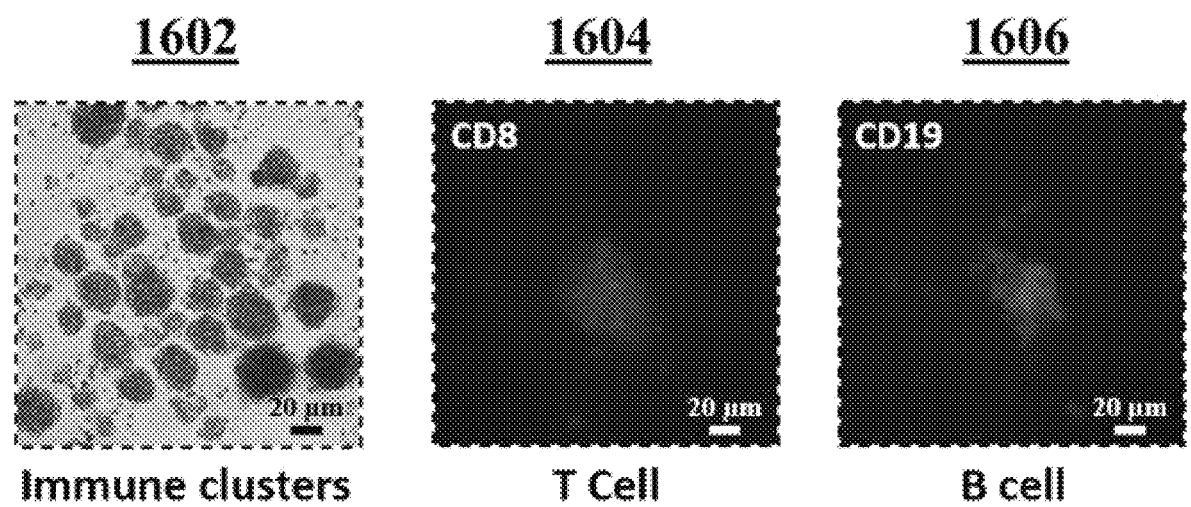
FIG. 16 shows images from an exemplary blood sample drawn from a COVID-19 infected patient representing activation and expansion of lymphocytes including immune clusters with immunofluorescence images from T cells clusters and from B cells clusters, consistent with one or more exemplary embodiments of the present disclosure.

Time-lapse imaging from samples of patients was done via immunofluorescence imaging. An exemplary sample was divided into two parts and each part was stained separately for analyzing and observing T cells clusters and B cells clusters separately. FIG. 16 shows images from an exemplary blood sample drawn from a COVID-19 infected patient representing activation and expansion of lymphocytes including immune clusters 1602 with immunofluorescence images 1604 from T cells clusters and 1606 from B cells clusters, consistent with one or more exemplary embodiments of the present disclosure. FIG. 16 reveals that lymphocyte clusters are formed in blood samples of patients due to cytokine storm.

Figure 17:
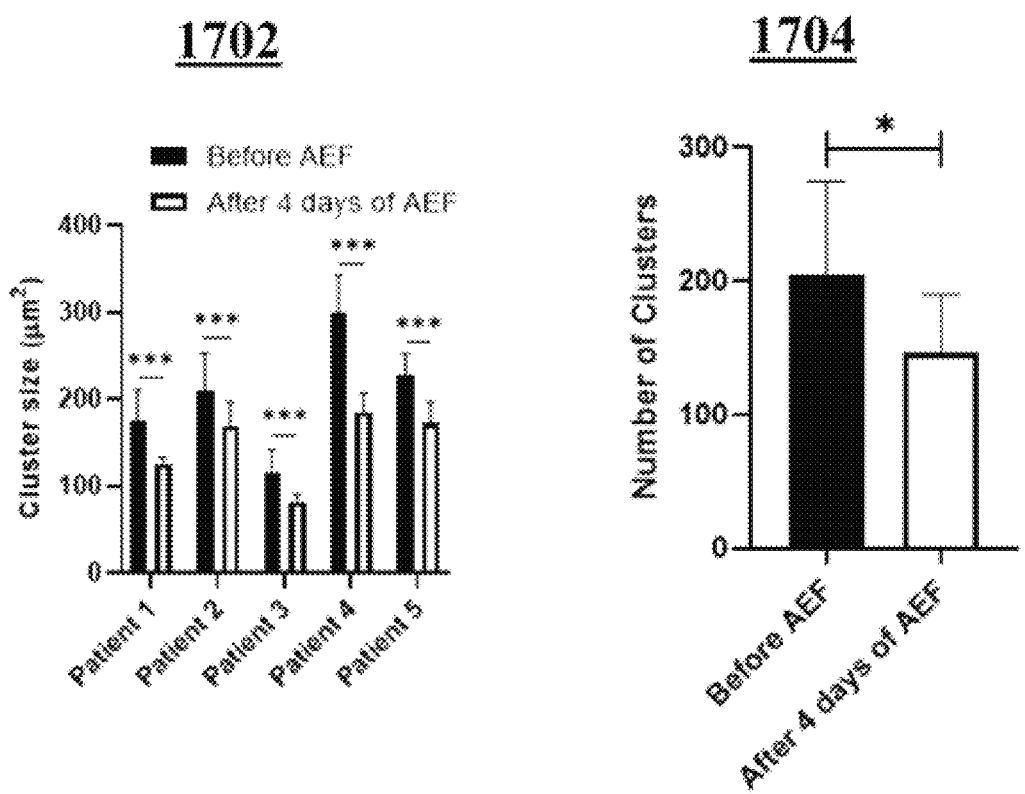
FIG. 17 shows mean clusters size and number of exemplary clusters before and after applying AEF, consistent with one or more exemplary embodiments of the present disclosure.

For AEF stimulation, lymphocytes were cultured in blood serums and were stimulated by AEF for 4 days. Size of produced clusters was analyzed after AEF stimulation. FIG. 17 shows mean clusters size (diagram 1702) and number of clusters (diagram 1704) before and after applying AEF, consistent with one or more exemplary embodiments of the present disclosure. Significant differences were observed in size of lymphocyte clusters after 4 days of AEF stimulation for COVID-19 patients PBMCs. Electrical stimulation halted growth of clusters in blood sample of each patient and also their average number was decreased by about 30%.

Figure 18:
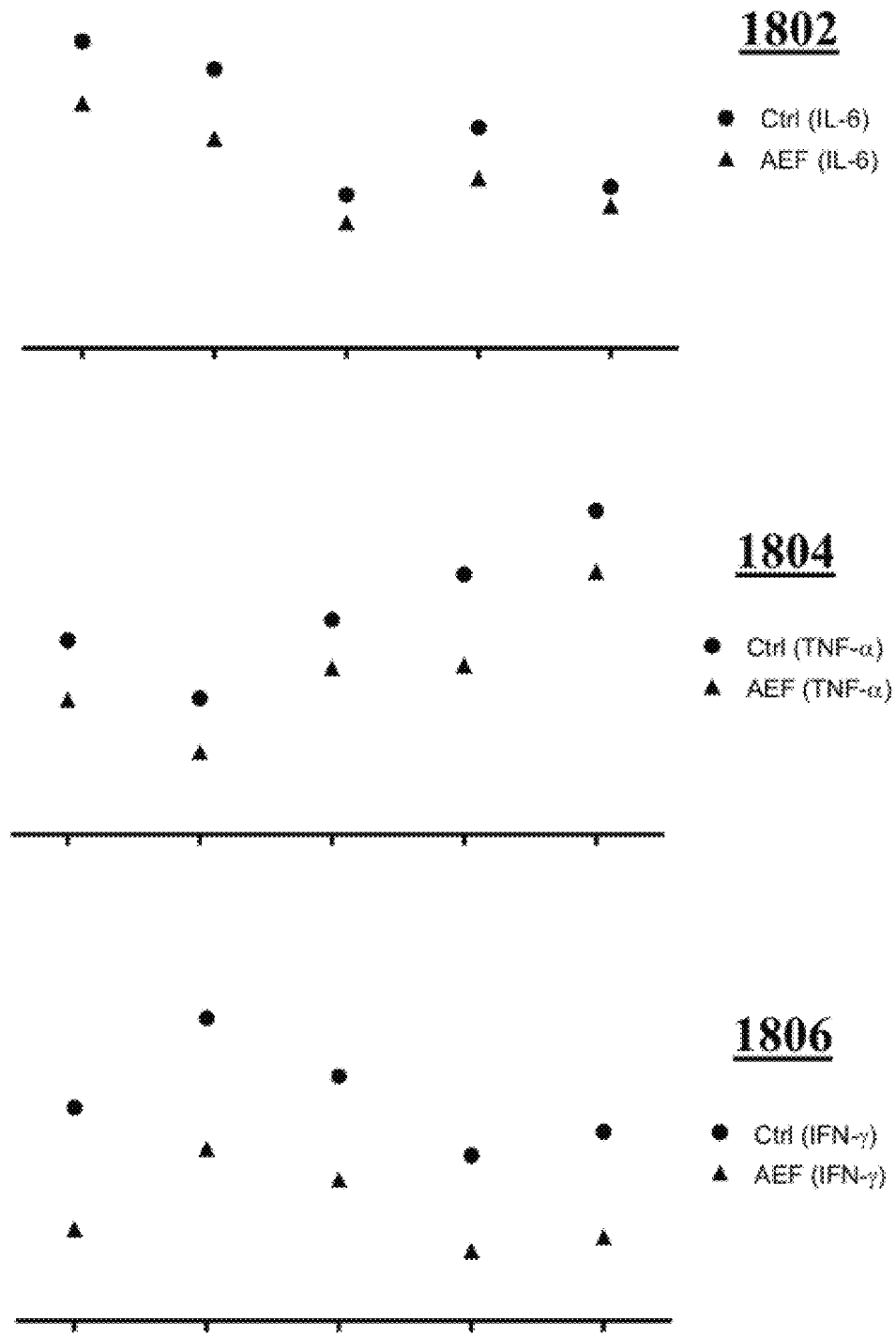
FIG. 18 shows concentration of inflammatory cytokines in exemplary COVID-19 patients' blood serum for control and AEF exposed groups, including IL-6, TNF-α, and IFN-γ, consistent with one or more exemplary embodiments of the present disclosure.

FIG. 18 shows concentration of inflammatory cytokines in COVID-19 patients' blood serum for control and AEF exposed groups, including IL-6 (diagram 1802), TNF-$\alpha$ (diagram 1804), and IFN-$\gamma$ (diagram 1806), consistent with one or more exemplary embodiments of the present disclosure. As presented in FIG. 18, all of three major cytokines in blood sample of all five patients were reduced after 4 days of AEF stimulation, even though an amount of reduction is different for each patient.

Figure 19:
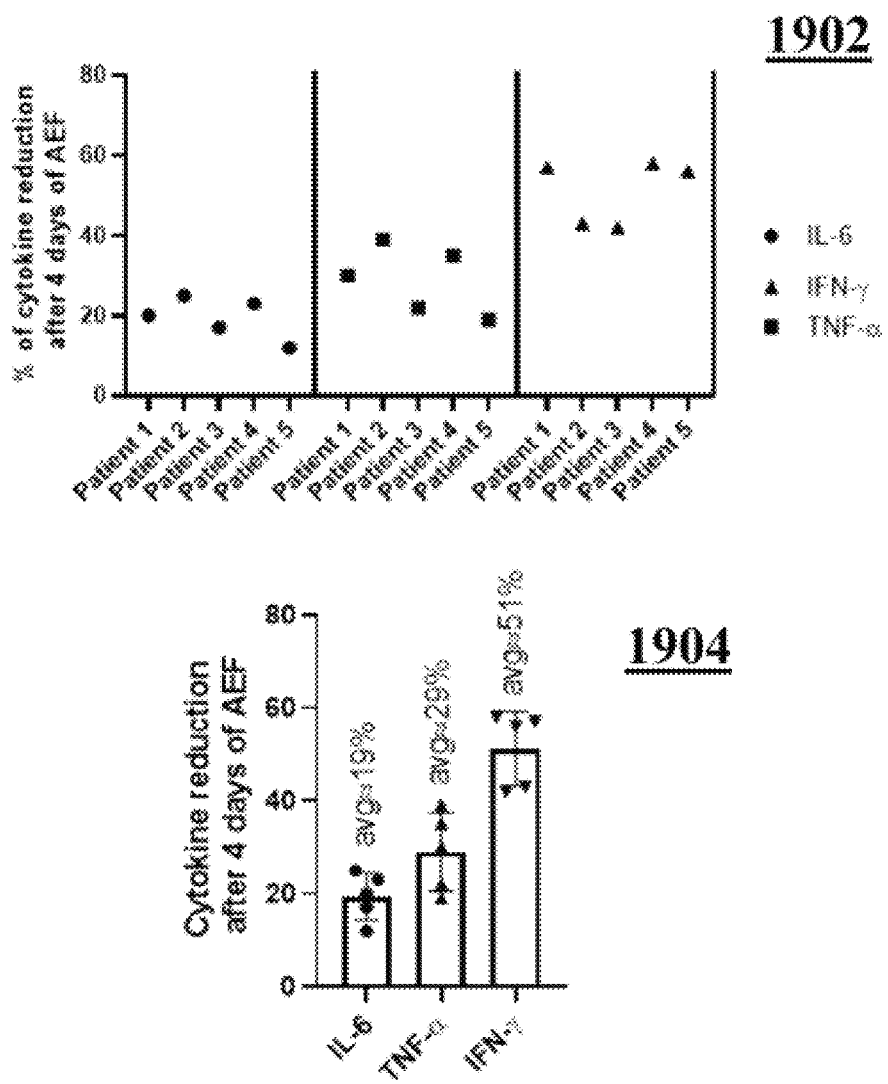
FIG. 19 shows percentage of cytokine reduction in exemplary COVID-19 patients' blood serum caused by AEF stimulation and average percentage of cytokine reduction in COVID-19 patients' blood serum after 4 days of exposure to AEF, consistent with one or more exemplary embodiments of the present disclosure.

FIG. 19 shows percentage of cytokine reduction in COVID-19 patients' blood serum caused by AEF stimulation (diagram 1902) and average percentage of cytokine reduction in COVID-19 patients' blood serum after 4 days of exposure to AEF (diagram 1904), consistent with one or more exemplary embodiments of the present disclosure. It may be seen that the most cytokine reduction is related to IFN-$\gamma$ by about 51%, while this number for TNF-$\alpha$ and IL-6 is about 29% and about 19%, respectively.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for preventing cytokine storm by suppressing clonal expansion of hyperactivated lymphocytes in a COVID-19 infected patient, the method comprising:
   placing at least four electrodes on skin of the COVID-19 infected patient by putting at least four electrodes over skin of the COVID-19 infected patient at respective four locations maximally 10 cm apart from a central part of an infected lung tissue of the COVID-19 infected patient, the infected lung tissue of the COVID-19 infected patient comprising a plurality of hyperactivated lymphocytes therein; and
   reducing an amount of inflammatory cytokines in bloodstream of the COVID-19 infected patient by suppressing mitosis of the hyperactivated proliferative lymphocytes cells within the infected lung tissue, the inflammatory cytokines comprising at least one of TNF-alpha, INF-gamma, IL-6, and combinations thereof, suppressing mitosis of the hyperactivated proliferative lymphocytes cells within the infected lung tissue comprising by electrically stimulating the hyperactivated proliferative lymphocytes therein, comprising:
      connecting the at least four electrodes to an AC function generator device;
      generating an alternating electric field (AEF) within the infected lung tissue by applying an AC voltage to the at least four electrodes utilizing the AC function generator device; and
      stimulating the hyperactivated proliferative lymphocytes with mitotic spindles aligned in a plurality of directions by periodically changing a direction of the generated AEF in the plurality of directions within the infected lung tissue, changing the direction of the generated AEF in the plurality of directions within the infected lung tissue comprising periodically stepwise changing a direction of the generated AEF by 45 degrees clockwise or counterclockwise per each time step of a plurality of time steps.

2. The method of claim 1, wherein suppressing mitosis of the hyperactivated proliferative lymphocytes cells within the infected lung tissue by electrically stimulating the hyperactivated proliferative lymphocytes is done for a pre-determined period of time comprising the plurality of time steps, the pre-determined period of time comprising at least 20 hours in form of at least one of a continuous time interval and a plurality of intermittent time intervals.

3. The method of claim 1, wherein periodically changing the direction of the generated AEF in the plurality of directions within the infected lung tissue comprises periodically switching of signal poles and ground poles of the applied AC voltage between at least two respective electrodes of the at least four electrodes at each time step of the plurality of time steps.

4. The method of claim 1, wherein each time step of the plurality of time steps comprises a time interval between 0.5 second and 5 seconds of the pre-determined period of time.

5. The method of claim 1, wherein placing the at least four electrodes on skin of the COVID-19 infected patient comprises placing at least four electrically conductive elements on skin of the COVID-19 infected patient with an area of each respective electrically conductive element being in a range between 1 cm$^2$ and 100 cm$^2$.

6. The method of claim 5, wherein placing the at least four electrodes on skin of the COVID-19 infected patient comprises placing at least four electrically conductive plates made of at least one of aluminum (Al), copper (Cu), stainless steel, gold (Au), chromium (Cr), Titanium (Ti), and combinations thereof on skin of the COVID-19 infected patient.

7. The method of claim 1, wherein applying the AC voltage to the at least four electrodes comprises applying an AC voltage in a range between 0.5 V/cm and 7 V/cm with a constant frequency in a range between 50 kHz and 200 kHz to the at least four electrodes.

8. The method of claim 1, wherein placing the at least four electrodes on skin of the COVID-19 infected patient comprises:
   putting a first electrode and a second electrode of the at least four electrodes on skin of the COVID-19 infected patient at two respective locations over chest in front of ribcage of the COVID-19 infected patient; and
   putting a third electrode and a fourth electrode of the at least four electrodes on skin of the COVID-19 infected patient at respective two locations maximally 10 cm apart from a central part of the infected lung tissue of the COVID-19 infected patient.

9. The method of claim 8, wherein putting the third electrode and the fourth electrode of the at least four electrodes on skin of the COVID-19 infected patient at the respective two locations maximally 10 cm apart from the central part of the infected lung tissue of the COVID-19 infected patient comprises putting the third electrode and the fourth electrode at respective two locations of skin placed over at least one of chest, armpit, waist, shoulder, back and combinations thereof of the COVID-19 infected patient.

10. The method of claim 1, wherein the each time step of the plurality of time steps comprises one second.

\* \* \* \* \*